(12) United States Patent
Campbell et al.

(10) Patent No.: US 11,007,219 B2
(45) Date of Patent: *May 18, 2021

(54) GUT-SELECTIVE SEQUESTERING AGENTS FOR THE TREATMENT AND PREVENTION OF AUTISM AND RELATED DISORDERS

(71) Applicant: Axial Biotherapeutics, Inc., Waltham, MA (US)

(72) Inventors: Anthony Stewart Campbell, Framingham, MA (US); David H. Donabedian, Providence, RI (US)

(73) Assignee: Axial Therapeutics, Inc., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/898,201

(22) Filed: Jun. 10, 2020

(65) Prior Publication Data
US 2020/0368276 A1    Nov. 26, 2020

Related U.S. Application Data

(63) Continuation of application No. 16/827,629, filed on Mar. 23, 2020, which is a continuation of application No. 15/994,571, filed on May 31, 2018, now Pat. No. 10,617,718, which is a continuation of application No. PCT/US2018/025607, filed on Mar. 31, 2018.

(60) Provisional application No. 62/480,039, filed on Mar. 31, 2017.

(51) Int. Cl.
| | | |
|---|---|---|
| A61K 33/44 | (2006.01) | |
| A61K 31/717 | (2006.01) | |
| A61P 25/22 | (2006.01) | |
| A61K 9/14 | (2006.01) | |
| A61K 33/06 | (2006.01) | |

(52) U.S. Cl.
CPC ............. *A61K 33/44* (2013.01); *A61K 9/14* (2013.01); *A61K 31/717* (2013.01); *A61K 33/06* (2013.01); *A61P 25/22* (2018.01)

(58) Field of Classification Search
None
See application file for complete search history.

(56) References Cited

U.S. PATENT DOCUMENTS

| | | |
|---|---|---|
| 4,681,764 A | 7/1987 | Endo et al. |
| 4,761,284 A | 8/1988 | Nishimura |
| 6,666,214 B2 | 12/2003 | Canham |
| 7,651,974 B2 | 1/2010 | Sonobe et al. |
| 8,309,130 B2 | 11/2012 | Sonobe et al. |
| 9,877,987 B2 | 1/2018 | Wakahoi et al. |
| 10,060,932 B2 | 8/2018 | West et al. |
| 10,617,718 B2 | 4/2020 | Campbell et al. |

(Continued)

OTHER PUBLICATIONS

U.S. Appl. No. 16/827,629, filed May 31, 2018, Campbell et al.

(Continued)

*Primary Examiner* — Isis A Ghali
(74) *Attorney, Agent, or Firm* — Wolf, Greenfield & Sacks, P.C.

(57) ABSTRACT

The present disclosure describes methods and compositions for the treatment of neurological disorders and related symptoms by the in vivo sequestration and excretion of microbial metabolites. These metabolites are related to neurological disorders such as autism and Parkinson's disease, as well as intestinal hyperpermeability (leaky gut) and gastrointestinal comorbidities associated with such disorders.

22 Claims, 7 Drawing Sheets

(56) References Cited

U.S. PATENT DOCUMENTS

| | | |
|---|---|---|
| 2014/0065132 A1 | 3/2014 | Hsiao et al. |
| 2014/0213534 A1 | 7/2014 | Waldman et al. |
| 2015/0064256 A1 | 3/2015 | Howell et al. |
| 2015/0111878 A1 | 4/2015 | Hoffman |
| 2016/0184293 A1 | 6/2016 | von Coburg et al. |
| 2016/0193169 A1 | 7/2016 | Hoffman |
| 2017/0020999 A1 | 1/2017 | Bathaei |
| 2018/0303876 A1 | 10/2018 | Campbell et al. |

OTHER PUBLICATIONS

PCT/US2018/025607, Jul. 12, 2018, International Search Report and Written Opinion.

PCT/US2018/025607, Oct. 10, 2018, International Preliminary Report on Patentability.

International Search Report and Written Opinion for Application No. PCT/US2018/025607 dated Jul. 12, 2018.

International Preliminary Report on Patentability for Application No. PCT/US2018/025607 dated Oct. 10, 2019.

[No Author Listed] Label for RISPERDAL® CONSTA®. 2007, revised Jun. 2009. Retrieved from the Internet: <https://www.accessdata.fda.gov/drugsatfda_docs/label/2009/020272-s056,020588s044,021346s033,021444s03lbl.pdf> on Mar. 7, 2019. 50 pages.

[No Author Listed] Label for ABILIFY®. Otsuka America Pharmaceutical, Inc. Revised Dec. 2014. 84 pages.

[No Author Listed] Label for RISPERDAL®. 2007, revised Jul. 2009. Retrieved from the Internet: <https://www.accessdata.fda.gov/drugsatfda_docs/label/2009/020272s056,020588s044,021346s033,021444s03lbl.pdf> on Mar. 7, 2019. 49 pages.

[No Author Listed] Prescribing Information for ABILIFY®. Otsuka America Pharmaceutical, Inc. Revised Aug. 2019. 88 pages.

[No Author Listed] Prescribing Information for RISPERDAL®. Janssen Pharmaceutical Ltd. Revised Jan. 2019. 58 pages.

Akiyama et al., A metabolomic approach to clarifying the effect of AST-120 on 5/6 nephrectomized rats by capillary electrophoresis with mass spectrometry (CE-MS). Toxins (Basel). Nov. 14, 2012;4(11):1309-22. doi: 10.3390/toxins4111309.

Aman et al., ABC-2: Aberrant Behavior Checklist, 2$^{nd}$ Ed. East Aurora, NY; Slosson. 2017. 142 pages.

Chen, Removal of fatty acids from serum albumin by charcoal treatment. J Biol Chem. Jan. 25, 1967;242(2):173-81.

Coretti et al., Gut Microbiota Features in Young Children With Autism Spectrum Disorders. Front Microbiol. Dec. 19, 2018;9:3146. doi: 10.3389/fmicb.2018.03146. eCollection 2018.

Crawley, Translational animal models of autism and neurodevelopmental disorders. Dialogues Clin Neurosci. Sep. 2012;14(3):293-305.

Czaja, Factoring the intestinal microbiome into the pathogenesis of autoimmune hepatitis. World J Gastroenterol. Nov. 14, 2016;22(42):9257-9278.

De Angelis et al., Autism spectrum disorders and intestinal microbiota. Gut Microbes. 2015;6(3):207-13. doi: 10.1080/19490976.2015.1035855.

Del Campo et al., The Use of Probiotic Therapy to Modulate the Gut Microbiota and Dendritic Cell Responses in Inflammatory Bowel Diseases. Med Sci (Basel). Feb. 22, 2019;7(2). pii: E33. doi: 10.3390/medsci7020033.

Dillon et al., Large surface area activated charcoal and the inhibition of aspirin absorption. Ann Emerg Med. May 1989;18(5):547-52.

Dorrestein et al., Finding the missing links among metabolites, microbes, and the host. Immunity. Jun. 19, 2014;40(6):824-32. doi: 10.1016/j.immuni.2014.05.015.

Fond et al., The "psychomicrobiotic": Targeting microbiota in major psychiatric disorders: A systematic review. Pathol Biol (Paris). Feb. 2015;63(1):35-42. doi: 10.1016/j.patbio.2014.10.003. Epub Nov. 2, 2014.

Gagnière et al., Gut microbiota imbalance and colorectal cancer. World J Gastroenterol. Jan. 14, 2016;22(2):501-18. doi: 10.3748/wjg.v22.i2.501.

Han et al., Gut Microbiota and Type 1 Diabetes. Int J Mol Sci. Mar. 27, 2018;19(4). pii: E995. doi: 10.3390/ijms19040995.

Hartmann et al., Alcoholic liver disease: the gut microbiome and liver cross talk. Alcohol Clin Exp Res. May 2015;39(5):763-75. doi: 10.1111/acer.12704. Author manuscript.

Horta-Baas et al., Intestinal Dysbiosis and Rheumatoid Arthritis: A Link between Gut Microbiota and the Pathogenesis of Rheumatoid Arthritis. J Immunol Res. 2017;2017:4835189. doi: 10.1155/2017/4835189. Epub Aug. 30, 2017.

Hsiao et al., Microbiota modulate behavioral and physiological abnormalities associated with neurodevelopmental disorders. Cell. Dec. 19, 2013;155(7):1451-63. doi: 10.1016/j.cell.2013.11.024. Epub Dec. 5, 2013.

Kang et al., Reduced incidence of Prevotella and other fermenters in intestinal microflora of autistic children. PLoS One. Jul. 3, 2013;8(7):e68322. doi: 10.1371/journal.pone.0068322. Print 2013.

Kieslichova et al., Acute Liver Failure due to Amanita phalloides Poisoning: Therapeutic Approach and Outcome. Transplant Proc. Jan.-Feb. 2018;50(1):192-197. doi: 10.1016/j.transproceed.2017.11.032.

Lau et al., Altered microbiome in chronic kidney disease: systemic effects of gut-derived uremic toxins. Clin Sci (Lond). Mar. 9, 2018;132(5):509-522. doi: 10.1042/CS20171107. Print Mar. 15, 2018.

Lerner et al., Changes in intestinal tight junction permeability associated with industrial food additives explain the rising incidence of autoimmune disease. Autoimmun Rev. Jun. 2015;14(6):479-89. doi: 10.1016/j.autrev.2015.01.009. Epub Feb. 9, 2015.

Lin et al., Role of intestinal microbiota and metabolites on gut homeostasis and human diseases. BMC Immunol. Jan. 6, 2017;18(1):2. doi: 10.1186/s12865-016-0187-3.

Liu et al, Altered composition and function of intestinal microbiota in autism spectrum disorders: a systematic review. Transl Psychiatry. Jan. 29, 2019;9(1):43. doi: 10.1038/s41398-019-0389-6.

Marcus et al., A placebo-controlled, fixed-dose study of aripiprazole in children and adolescents with irritability associated with autistic disorder. J Am Acad Child Adolesc Psychiatry. 2009;48(11):1110-1119. doi:10.1097/CHI.0b013e3181b76658.

Mendez-Figueroa et al., Can Gut Microbiota and Lifestyle Help Us in the Handling of Anorexia Nervosa Patients? Microorganisms. Feb. 22, 2019;7(2). pii: E58. doi: 10.3390/microorganisms7020058.

Mokhlesi et al., Toxicology in the critically ill patient. Clin Chest Med. Dec. 2003;24(4):689-711.

Ni et al., Gut microbiota and IBD: causation or correlation? Nat Rev Gastroenterol Hepatol. Oct. 2017;14(10):573-584. doi: 10.1038/nrgastro.2017.88. Epub Jul. 19, 2017. Author manuscript.

Ohkusa et al., Gut Microbiota and Chronic Constipation: A Review and Update. Front Med (Lausanne). Feb. 12, 2019;6:19. doi: 10.3389/fmed.2019.00019. eCollection 2019.

Peterson et al Immune homeostasis, dysbiosis and therapeutic modulation of the gut microbiota. Clin Exp Immunol. Mar. 2015;179(3):363-77. doi: 10.1111/cei.12474.

Rosenfeld, Microbiome Disturbances and Autism Spectrum Disorders. Drug Metab Dispos. Oct. 2015;43(10):1557-71. doi: 10.1124/dmd.115.063826. Epub Apr. 7, 2015.

Scheperjans, The prodromal microbiome. Mov Disord. Jan. 2018;33(1):5-7. doi: 10.1002/mds.27197. Epub Oct. 30, 2017.

Schippa et al., Dysbiotic events in gut microbiota: impact on human health. Nutrients. Dec. 11, 2014;6(12):5786-805. doi: 10.3390/nu6125786.

Schulman et al., The effects of AST-120 on chronic kidney disease progression in the United States of America: a post hoc subgroup analysis of randomized controlled trials. BMC Nephrol. Sep. 30, 2016;17(1):141.

Smith et al., Amino Acid Dysregulation Metabotypes: Potential Biomarkers for Diagnosis and Individualized Treatment for Subtypes of Autism Spectrum Disorder. Biol Psychiatry. Feb. 15, 2019;85(4):345-354. doi: 10.1016/j.biopsych.2018.08.016. Epub Sep. 6, 2018.

(56) References Cited

OTHER PUBLICATIONS

Spor et al., Unravelling the effects of the environment and host genotype on the gut microbiome. Nat Rev Microbiol. Apr. 2011;9(4):279-90. doi: 10.1038/nrmicro2540.

Thursby et al., Introduction to the human gut microbiota. Biochem J. May 16, 2017;474(11):1823-1836. doi: 10.1042/BCJ20160510.

Tomasello et al., Nutrition, oxidative stress and intestinal dysbiosis: Influence of diet on gut microbiota in inflammatory bowel diseases. Biomed Pap Med Fac Univ Palacky Olomouc Czech Repub. Dec. 2016;160(4):461-466. doi: 10.5507/bp.2016.052. Epub Oct. 26, 2016.

Wieland et al., Systematic review: microbial dysbiosis and nonalcoholic fatty liver disease. Aliment Pharmacol Ther. Nov. 2015;42(9):1051-63. doi: 10.1111/apt.13376. Epub Aug. 24, 2015.

Yamaguchi et al., Effect of AST-120 in Chronic Kidney Disease Treatment: Still a Controversy? Nephron. 2017;135(3):201-206. doi: 10.1159/000453673. Epub Dec. 14, 2016.

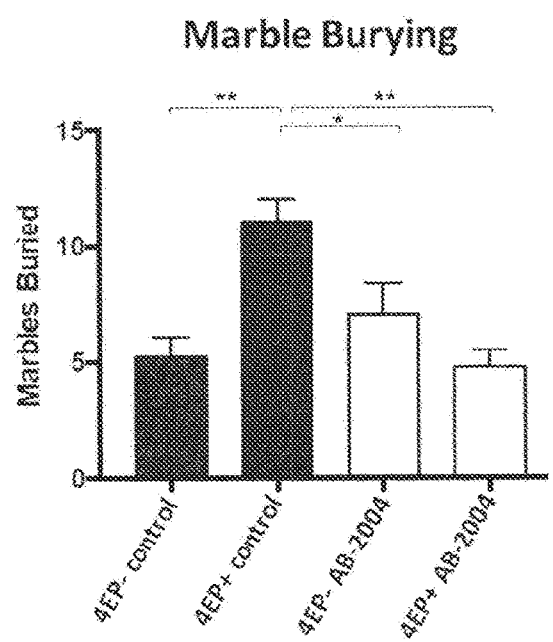
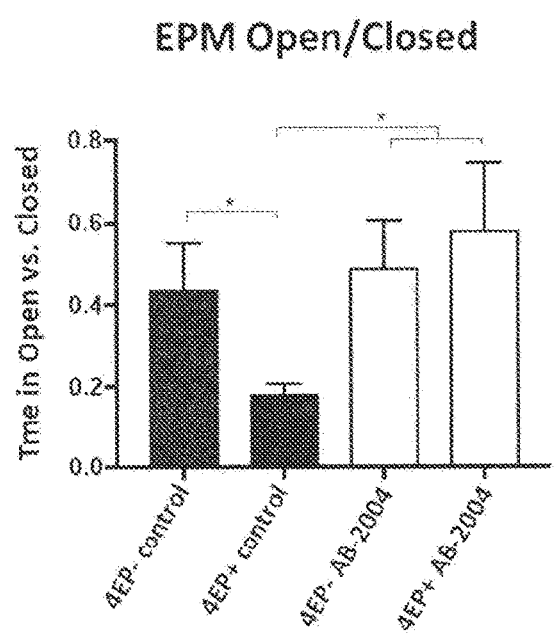
Fig. 3A
Fig. 3B

GUT-SELECTIVE SEQUESTERING AGENTS FOR THE TREATMENT AND PREVENTION OF AUTISM AND RELATED DISORDERS

CROSS REFERENCE TO RELATED APPLICATIONS

This application is a continuation of U.S. application Ser. No. 16/827,629, filed Mar. 23, 2020, which is a continuation of U.S. application Ser. No. 15/994,571, filed May 31, 2018, which is a continuation of International Application No. PCT/US2018/025607, filed Mar. 31, 2018 which claims the benefit of U.S. Provisional Application Ser. No. 62/480,039, filed Mar. 31, 2017, each of which is hereby expressly incorporated by reference in its entirety.

FIELD

The present disclosure relates to methods of treating, inhibiting, or ameliorating a behavioral symptoms of a neurological disorder, such as autism, and associated pathologies including intestinal hyperpermeability or leaky gut.

BACKGROUND

Non-absorbable, non-digestible, biocompatible polymers have been used for lowering cholesterol and systemic phosphate levels by targeting adsorption of cholesterol and free phosphate in the gut. These products are biocompatible ion exchange resins that are not absorbed to any significant extent and are excreted from the gastrointestinal (GI) tract after binding their target molecules. For example, the ion exchange resin, cholestyramine, has been used for sequestering bile acids, which are cholesterol derivatives, so as to lower cholesterol. Additionally, non-absorbable, non-digestible, biocompatible activated carbon preparations have been investigated to counteract the effects of toxins in poisoning and drug overdoses (e.g., Dillon et al. (1989), *Ann. Emerg. Med.* 18(5):547-52; Kieslichova et al. (2018), *Transplantation Proc.* 50:192-197), and uremic toxins in the treatment of chronic kidney disease (e.g., Schulman et al. (2016), *BMC Nephrology* 17:141). For example, an activated carbon particle preparation has been developed and utilized for delaying dialysis in subjects suffering from chronic kidney disease, but the clinical utility of this approach has not been roundly accepted, multiple meta-analyses have indicated no clear clinical benefit, and a later stage clinical trial in the US failed to prove efficacy.

SUMMARY

In one aspect, the invention provides sequestrant compositions for use in the treatment of a subject having a behavioral symptom of a neurological disorder associated with intestinal hyperpermeability (or leaky gut) or intestinal dysbiosis. These compositions comprise a multiplicity of biocompatible particles and/or polymers which are non-digestible and non-absorbable by the digestive tract of the subject. The sequestrant compositions bind to at least a fraction of at least one intestinal metabolite present in the digestive tract of the subject to form a sequestrant-metabolite complex, which may include covalent or non-covalent bonds. As a result of the formation of the sequestrant-metabolite complex, the intestinal metabolite is eliminated from the digestive tract along with the sequestrant composition, rather than interacting with or being absorbed by the tissues of the digestive tract. The intestinal metabolites which are bound by the sequestrant compositions are associated with the development or presence of the behavioral symptom and, thus, the elimination of the intestinal metabolite aids in the treatment of the behavioral symptom and neurological disorder.

In another aspect, the invention provides methods of treating a subject having a behavioral symptom of a neurological disorder associated with intestinal hyperpermeability or intestinal dysbiosis. These methods comprise administering to the subject a sequestrant composition of the invention which binds to at least a fraction of at least one intestinal metabolite present in the digestive tract of the subject. As described above, the sequestrant and metabolite form a sequestrant-metabolite complex, such that the intestinal metabolite is eliminated from the digestive tract along with the sequestrant composition, rather than interacting with or being absorbed by the tissues of the digestive tract. Because the intestinal metabolites are associated with the development or presence of the behavioral symptom, the binding of the sequestrant compositions promotes the elimination of the intestinal metabolite and aids in the treatment of the behavioral symptom and neurological disorder.

In another aspect, the invention provides methods of reducing the amount of one or more intestinal metabolites from a subject having a behavioral symptom of a neurological disorder associated with intestinal hyperpermeability or intestinal dysbiosis. The methods comprise administering to the subject a sequestrant composition which binds to at least a fraction of at least one intestinal metabolite present in the digestive tract of the subject. As described above, the sequestrant and intestinal metabolite form a sequestrant-metabolite complex, such that the intestinal metabolite is eliminated from the digestive tract along with the sequestrant composition, rather than interacting with or being absorbed by the tissues of the digestive tract. Thus, the binding of the sequestrant compositions to intestinal metabolites which are associated with the development or presence of the behavioral symptom promotes the elimination of the intestinal metabolites and aids in the treatment of the behavioral symptom and neurological disorder.

In each of the foregoing aspects, in some embodiments the sequestrant composition comprises a multiplicity of particles which are biocompatible with, non-digestible by, and/or non-absorbable by the digestive tract of the subject.

In each of the foregoing aspects, in some embodiments, the sequestrant composition comprises activated carbon particles, a clay, an apatite or hydroxyapatite, a bentonite, a kaolin, a pectin, a cellulose polymer, a cellulose acetate polymer, a cellulose acetate propionate, an ion exchange resin, a cholestyramine polymer, a tetraethylenepentamine polymer, a phenolic resin, a boronic acid-presenting polymer, a catechin-presenting polymer, or a zeolite.

In each of the foregoing aspects, in some embodiments, the sequestrant composition comprises an AB-2004 preparation. The AB-2004 compositions of the invention comprise spherical activated carbon particles. In some embodiments, the spherical activated carbon particles have a minimum average specific surface area determined by the Brunauer-Emmett-Teller (BET) method of at least 500 $m^2/g$ and a maximum average specific surface area determined by the Brunauer-Emmett-Teller (BET) method less than 4000 $m^2/g$. In some embodiments, the spherical activated carbon particles have a minimum average particle diameter of at least 0.005 and a maximum average particle diameter of less than 1.5 mm. In some embodiments, the spherical activated carbon particles have both (a) a minimum average specific surface area determined by the Brunauer-Emmett-Teller (BET) method of at least 500 m²/g and a maximum average specific surface area determined by the Brunauer-Emmett-Teller (BET) method less than 4000 m²/g, and (b) a minimum average particle diameter of at least 0.005 and a maximum average particle diameter of less than 1.5 mm.

In each of the foregoing aspects, in some embodiments, the sequestrant composition of the invention is formulated for controlled release in the lower digestive tract. Such compositions can be administered orally or as a suppository.

In each of the foregoing aspects, in each of the foregoing embodiments, the neurological disorder can be selected from any of: autism spectrum disorder, an anxiety disorder, Parkinson's Disease, Rett Syndrome, Fragile X Syndrome, Tuberous Sclerosis, Multiple Sclerosis, Alzheimer's Disease, Angelman Syndrome, Williams Syndrome, amyotrophic lateral sclerosis, leukodystrophies including Alexander Syndrome, alpha-synucleinopathies including Lewy Body Dementia, incidental Lewy body disease, Lewy body variant of Alzheimer's disease, multiple system atrophy, pure autonomic failure, or any combination thereof.

In each of the foregoing aspects, in some embodiments, the behavioral symptom is selected from: tremors, paralysis, dyskinesia, repetitive behaviors, communicative symptoms, cognitive disorders, stereotyped behaviors, attachment to physical objects, aphasia, obsessive behaviors, unusual or inappropriate body language, gestures, and/or facial expressions and/or sensorimotor issues, lack of interest in other people, lack of empathy, difficulty grasping nonverbal cues, touch aversion, difficulty in socialization, speech delays, abnormal vocal tone or pitch, vocal repetition, perseveration, conversational difficulty, difficulty communicating needs or desires, inability to understand simple statements or questions, difficulties in processing language subtext, obsessive attachment to unusual objects, preoccupation, intolerance of changes in routine or environment, clumsiness, abnormal posture, odd ways of moving, fascination with particular objects, hyper- or hypo-reactivity to sensory input, and clinical irritability.

In each of the foregoing aspects, in some embodiments, the neurological disorder is autism spectrum disorder and the behavioral symptom is selected from: repetitive behaviors, communicative symptoms, stereotyped behaviors, and clinical irritability.

In each of the foregoing aspects, in some embodiments, the subject does not have clinical anxiety or an anxiety disorder.

In each of the foregoing aspects, in some embodiments, the subject does not have chronic kidney disease.

In each of the foregoing aspects, in some embodiments, the intestinal metabolite is selected from: 4-ethylphenol (4-EP), 4-ethylphenylsulfate (4-EPS), p-cresol (PC), p-cresyl sulfate (PCS), 3-indoxyl sulfate, 3-hydroxy indole, coumaric acid, 3-(3-hydroxyphenyl)-3-hydroxypropionic acid (HPHPA), 3-(3-hydroxyphenyl)propanoic acid, 3-(4-hydroxy-phenyl)propanoic acid, 3-hydroxy hippuric acid (3HHA), 3-carboxy-4-methyl-5-propyl-2-furanoic acid (CMPF), 3-hydroxyphenyl acetic acid (3HPA), 4-hydroxyphenyl acetic acid, and 2-hydroxy-2-(4-hydroxyphenyl)acetic acid.

In each of the foregoing aspects, in some embodiments, the intestinal metabolite is selected from the group consisting of: 4-ethylphenol (4-EP), 4-ethylphenylsulfate (4-EPS), p-cresol (PC), p-cresyl sulfate (PCS), 3-hydroxy indole, and 3-indoxyl sulfate.

In each of the foregoing aspects, in some embodiments, the method of treatment comprises monitoring intestinal metabolite levels of the subject during the course of treatment.

In each of the foregoing aspects, in some embodiments, the method of treatment comprises monitoring changes in the behavior of the subject.

In each of the foregoing aspects, in some embodiments, the method of treatment comprises administering the sequestrant composition following the appearance of behavioral symptoms of the neurological disorder.

In each of the foregoing aspects, in some embodiments, the method of treatment comprises administering the sequestrant composition prior the appearance of behavioral symptoms of the neurological disorder.

In each of the foregoing aspects, in some embodiments, the method of treatment is repeated as necessary to maintain reduced levels of intestinal metabolites relative to the levels identified prior to the first administration of the composition. In some embodiments, for a given administration, the composition is different from a composition previously administered.

In each of the foregoing aspects, in some embodiments, the method of treatment comprises monitoring changes in the behavior of the subject.

Thus, described herein are methods for the treatment, inhibition, or amelioration of one or more or a plurality of neurological disorders, leaky gut comorbid with a neurological disorder, or leaky gut independent of a neurological disorder, associated with alterations in the intestinal microbiome. In some embodiments, the methods comprise the step of administering to a subject a composition that sequesters intestinal metabolites associated with alterations in the intestinal microbiome and, after having sequestered the intestinal metabolites, is eliminated from the digestive tract without being metabolized. In some embodiments, the methods further comprise the step of identifying and/or selecting a subject having elevated levels of one or more intestinal metabolites associated with alterations in the intestinal microbiome, having symptoms of a disorder associated with alterations in the intestinal microbiome, diagnosed with a disorder associated with alterations in the intestinal microbiome, or at increased risk of developing a disorder associated with alterations in the intestinal microbiome. The compositions to be administered according to the methods of the present disclosure may comprise an adsorbent, polymer, clay, or resin, which may comprise, consist essentially of, or consist of one or more of an activated carbon, an apatite or hydroxyapatite, a bentonite, a kaolin, a pectin, a cellulose polymer, a cellulose acetate polymer, a cellulose acetate propionate, an ion exchange resin, a cholestyramine polymer, a tetraethylenepentamine polymer, a phenolic resin, a boronic acid-presenting polymer, a catechin-presenting polymer, a zeolite, and/or a nanoparticle, or any combination thereof. The compositions to be administered according to the methods of the present disclosure may comprise, consist essentially of, or consist of preparations of high surface-area activated-carbon particles referred to as AB-2004 herein. The compositions to be administered according to the methods of the present disclosure may further be formulated for controlled release in the lower gastrointestinal tract.

The methods of the present disclosure can be applied to address one or more or a plurality of neurological disorders, e.g., one or more of autism spectrum disorder, schizophrenia, an anxiety disorder, depression, Parkinson's Disease, Rett Syndrome, Fragile X Syndrome, Tuberous Sclerosis, Multiple Sclerosis, Alzheimer's Disease, Angelman Syndrome, Williams Syndrome, amyotrophic lateral sclerosis, leukodystrophies including Alexander Syndrome, alpha-synucleinopathies including Lewy Body Dementia, incidental Lewy body disease, Lewy body variant of Alzheimer's disease, multiple system atrophy, pure autonomic failure, or any combination thereof. The methods of the present disclosure may further be applied to address a neurological disorder, wherein the neurological disorder presents a leaky gut (intestinal hyperpermeability) in said subject, as well as leaky gut symptoms associated with such neurological disorders, and/or leaky gut symptoms not associated with a neurological disorder.

The methods according to the present disclosure promote the sequestration of intestinal metabolites associated with intestinal hyperpermeability (leaky gut) or intestinal dysbiosis (i.e., deleterious changes in the intestinal microbiome), including both microbial metabolites and products of host metabolism of microbial metabolites. Such intestinal metabolites include, without limitation, those generated from the metabolism of tryptophan (e.g., serotonin, 5-hydroxyindoleacetate, kynurenine, kynurenate, anthranilate, xanthurenate, quinolinate, nicotinate, nicotinamide, indole, 3-hydroxy indole, 3-indoxyl sulfate, indole pyruvate, indole propionate, indole acetate, tryptamine), those generated from the metabolism of tyrosine (e.g., 4-ethylphenol (4-EP), 4-ethylphenylsulfate (4-EPS), p-cresol (PC), p-cresyl sulfate (PCS), 4-hydroxyphenylacetate, 2-hydroxy-2(4-hydroxyphenyl)acetate, homocitrulline), and those generated from the metabolism of benzoate (e.g., benzoate, hippurate, catechol, catechol sulfate), as well as N-acetylserine, beta-alanine, glutamine, transurocanate, imidazole propionate, phenylacetylglycine, phenol, phenyl sulfate, coumaric acid, 3-(3-hydroxyphenyl)-3-hydroxypropionic acid (HPHPA), 3-(3-hydroxyphenyl)propanoic acid, 3-(4-hydroxyphenyl) propanoic acid, 3-hydroxy hippuric acid (3HHA), 3-carboxy-4-methyl-5-propyl-2-furanoic acid (CMPF), 3-hydroxyphenyl acetic acid (3HPA), 3-methyl-2-oxovalerate, 4-methyl-2-oxopentaoate, cysteine, arginine, ornithine, 5-methylthioadenosine, glycylvaline, Fibrinogen Cleavage Peptide, 3-phosphoglycerate, phosphoenolpyruvate, ribose, xylose, docosapentaenoate (n3 DPA; 22:5n3), docosapentaenoate (n6 DPA; 22:5n6), docosahexaenoate (DHA; 22:6n3), stearate, eicosenoate, dihomo-linoleate (20:2n6), adrenate, 13-HODE+9-HODE, octadecanedioate, 12-HETE, myo-inositol, 1-palmitoylglycerophosphoethanolamine, N-alpha-acetyl-1-arginine, methyl guanidine, phenylacetylglutamine, indole-3-acetic acid, indole lactate, 1-oleoylglycerophosphoethanolamine, 1-pentadecanoylglycero-phosphocholine, 1-palmitoleoylglycerophosphocholine, 1-stearoylglycerophosphoinositol, 1-palmitoylplasmenylethanolamine, bilirubin (E,E), pantothenate, glycolate (hydroxyacetate), ergothioneine, equol, and/or equol sulfate, or any combination thereof.

Without being bound by any theory, in some embodiments, a microbial metabolite results from a metabolic pathway involving tyrosine. In some embodiments, said microbial metabolite is p-cresol. In some embodiments, said microbial metabolite is 4-ethyl phenol. In some embodiments, said metabolite is p-cresol sulfate. In some embodiments, said microbial metabolite is 4-ethyl phenyl sulfate.

Without being bound by any theory, in some embodiments, a microbial metabolite is an aromatic or heteroaromatic alcohol or sulfate thereof, resulting from the sulfation or sulfonation of said aromatic or heteroaromatic alcohol. In some embodiments, the aromatic alcohol is p-cresol. In some embodiments, the aromatic alcohol is 4-ethyl phenol. In some embodiments, the aromatic sulfate is 4-ethyl phenyl sulfate.

In some embodiments, said aromatic or heteroaromatic alcohol or sulfate thereof is monocyclic. In some embodiments, said aromatic or heteroaromatic alcohol is bicyclic, tricyclic, or polycyclic. In some embodiments, the heteroaromatic bicyclic alcohol is 3-hydroxy indole. In some embodiments the heteroaromatic bicyclic sulfate is 3-indoxyl sulfate.

The terms "aromatic", "heteroaromatic", "alcohol", "sulfate", "sulfation", "sulfonation", "monocyclic", "bicyclic", and "polycyclic" are art-recognized terms of organic chemistry, medicinal chemistry, or pharmaceutical chemistry, and would be readily recognized as such by a person of ordinary skill in the art of organic chemistry, medicinal chemistry, or pharmaceutical chemistry.

As used herein, "aromatic" groups (or "aryl" or "arylene" groups) include aromatic carbocyclic ring systems (e.g., phenyl) and fused polycyclic aromatic ring systems (e.g., naphthyl, biphenyl, and 1,2,3,4-tetrandronaphthyl).

The terms "heteroaryl", "heteroaromatic" or "heteroarylene" as used herein, include aromatic ring systems, including, but not limited to, monocyclic, bicyclic and tricyclic rings, and have 5 to 12 atoms including at least one heteroatom, such as nitrogen, oxygen, or sulfur. For purposes of exemplification, which should not be construed as limiting the scope of this invention: azaindolyl, benzo(b) thienyl, benzimidazolyl, benzofuranyl, benzoxazolyl, benzothiazolyl, benzothiadiazolyl, benzoxadiazolyl, furanyl, imidazolyl, imidazopyridinyl, indolyl, indazolyl, isoxazolyl, isothiazolyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrazolyl, thiadiazolyl, thienyl, 6H-pyrrolo[2,3-e][1,2,4]triazolo[4,3-a]pyrazinyl, 6H-imidazo[1,5-a]pyrrolo[2,3-e]pyrazinyl, 1,6-dihydropyrazolo[3,4-d]pyrrolo[2,3-b]pyridine, 3H-3,4,6,8a-tetraaza-asindacenyl, 3H-imidazo[1,2-a]pyrrolo[2,3-e]pyrazinyl, pyrazolo[3,4-d]pyrrolo[2,3-b]pyridinyl, 1,6-dihydro-1,2,5,6-tetraza-as-indacenyl, 3H-3,4,8a-triaza-as-indacenyl, 6H-3-oxa-2,5,6-triaza-as-indacenyl, 3,6-dihydro-2,3,6-tetraaza-as-indacenyl, 1,6-dihydro-dipyrrolo[2,3-b; 2'3'-d]pyridinyl, 6H-3-thia-2,5,6-triaza-as-indacenyl, 4,5-dihydro-1H-benzo[b]azepin-2(3H)-one, 3,4-dihydroquinolin-2 (1H)-one, 2H-benzo[b][1,4]oxazin-3(4H)-one, or 6,7-dihydro-4H-pyrazolo[5,1-c][1,4]oxazinyl or 1,6-dihydroimidazo[4,5-d]pyrrolo[2,3-b]pyridine.

The methods according to the present disclosure may comprise dosing schedules wherein at least one of the sequestrant compositions disclosed herein is administered multiple times per day, daily, or less frequently than daily. According to the methods described herein, dosing of the disclosed compositions may occur every second day, every third day, every fourth day, every fifth day, every sixth day, or every seventh day. According to the methods described herein, dosing may initiate prior to, concurrent with, or following the appearance of one or more or a plurality of symptoms of a neurological disorder, such as autism and/or associated pathologies including intestinal hyperpermeability (leaky gut) in a subject. The methods as described herein may also incorporate monitoring or a determining of one or more microbial metabolite levels, changes in behavior, and/or changes in gastrointestinal symptoms in a subject before, during, or after the course of therapy.

The methods described herein can be repeated as necessary to treat or prevent one or more of a plurality of symptoms of a neurological disorder, as well as leaky gut symptoms associated with such neurological disorders, and/or leaky gut symptoms not associated with a neurological disorder, and/or to maintain reduced levels of intestinal metabolites relative to the levels identified prior to the first administration of the composition. For each administration according to the methods described herein, the composition can be the same as a composition previously administered or can be different from a composition previously administered.

In some embodiments, a neurological disorder as contemplated herein comprises one or more symptoms selected from the group consisting of: tremors, paralysis, dyskinesia, repetitive behaviors, communicative symptoms, cognitive disorders, stereotyped behaviors, attachment to physical objects, aphasia, obsessive behaviors, unusual or inappropriate body language, gestures, and/or facial expressions and/or sensorimotor issues, lack of interest in other people, lack of empathy, difficulty grasping nonverbal cues, touch aversion, difficulty in socialization, speech delays, abnormal vocal tone or pitch, vocal repetition, perseveration, conversational difficulty, difficulty communicating needs or desires, inability to understand simple statements or questions, difficulties in processing language subtext, obsessive attachment to unusual objects, preoccupation, intolerance of changes in routine or environment, clumsiness, abnormal posture, odd ways of moving, fascination with particular objects, and hyper- or hypo-reactivity to sensory input, clinical irritability or any combination thereof. In some embodiments, the neurological disorder comprises one or more of autism spectrum disorder, schizophrenia, an anxiety disorder, depression, Parkinson's Disease, Rett Syndrome, Fragile X Syndrome, Tuberous Sclerosis, Multiple Sclerosis, Alzheimer's Disease, Angelman Syndrome, Williams Syndrome, amyotrophic lateral sclerosis, leukodystrophies including Alexander Syndrome, alpha-synucleinopathies including Lewy Body Dementia, incidental Lewy body disease, Lewy body variant of Alzheimer's disease, multiple system atrophy, pure autonomic failure, or any combination thereof. In some embodiments, the neurological disorder may comprise autism spectrum disorder that comprises a symptom other than clinical anxiety. In some embodiments, the neurological disorder does not comprise an anxiety disorder. In some embodiments, the neurological disorder may comprise autism spectrum disorder that comprises clinical irritability symptoms.

In some embodiments, the methods provided may further comprise monitoring, after said administering, changes in a symptom selected from the group consisting of: tremors, paralysis, dyskinesia, repetitive behaviors, communicative symptoms, cognitive disorders, stereotyped behaviors, attachment to physical objects, aphasia, obsessive behaviors, unusual or inappropriate body language, gestures, and/or facial expressions and/or sensorimotor issues, lack of interest in other people, lack of empathy, difficulty grasping nonverbal cues, touch aversion, difficulty in socialization, speech delays, abnormal vocal tone or pitch, vocal repetition, perseveration, conversational difficulty, difficulty communicating needs or desires, inability to understand simple statements or questions, difficulties in processing language subtext, obsessive attachment to unusual objects, preoccupation, intolerance of changes in routine or environment, clumsiness, abnormal posture, odd ways of moving, fascination with particular objects, and hyper- or hypo-reactivity to sensory input, clinical irritability or any combination thereof.

In some embodiments, the neurological disorder comprises autism spectrum disorder, and the methods as described herein further comprise monitoring the amelioration of a symptom of autism spectrum disorder other than clinical anxiety following the administration of a composition as described herein. In some embodiments, the symptoms of autism spectrum disorder comprise one or more of the following: repetitive behaviors, communicative symptoms, cognitive disorders, difficulty in socialization, and irritability. In some embodiments, the sequestrant composition to be administered comprises an AB-2004 preparation.

BRIEF DESCRIPTION OF THE DRAWINGS

FIGS. 3A-3B show that administration of an AB-2004 preparation normalizes repetitive and anxiety-like behaviors. (FIG. 3A) Marble burying test of repetitive behavior. (FIG. 3B) Elevated plus maze test of exploratory behavior (* indicates $p<0.05$, ** indicates $p<0.01$. Mean+/−Standard Deviation).

(FIG. 4A) Frequency with which mice entered wall area of the open field, as a percentage of total combined entries into the wall area and the center area. (FIG. 4B) Total duration in the wall area (seconds). (FIG. 4C) Total distance moved during the test (cm).

FIGS. 5A-5B show the results of a three chamber test of direct social interaction. Time spent in chamber with another mouse by: (FIG. 5A) male mice on control diet with microbiota that do not produce 4EP (left bar) and that do produce 4-EP (right bar); and (FIG. 5B) male mice with 4-EP producing microbiota on control diet (left bar) and diet containing an AB-2004 preparation (right bar). (**$p<0.01$; Mean+/−Standard Error of the Mean shown.)

DETAILED DESCRIPTION

Figure 1:
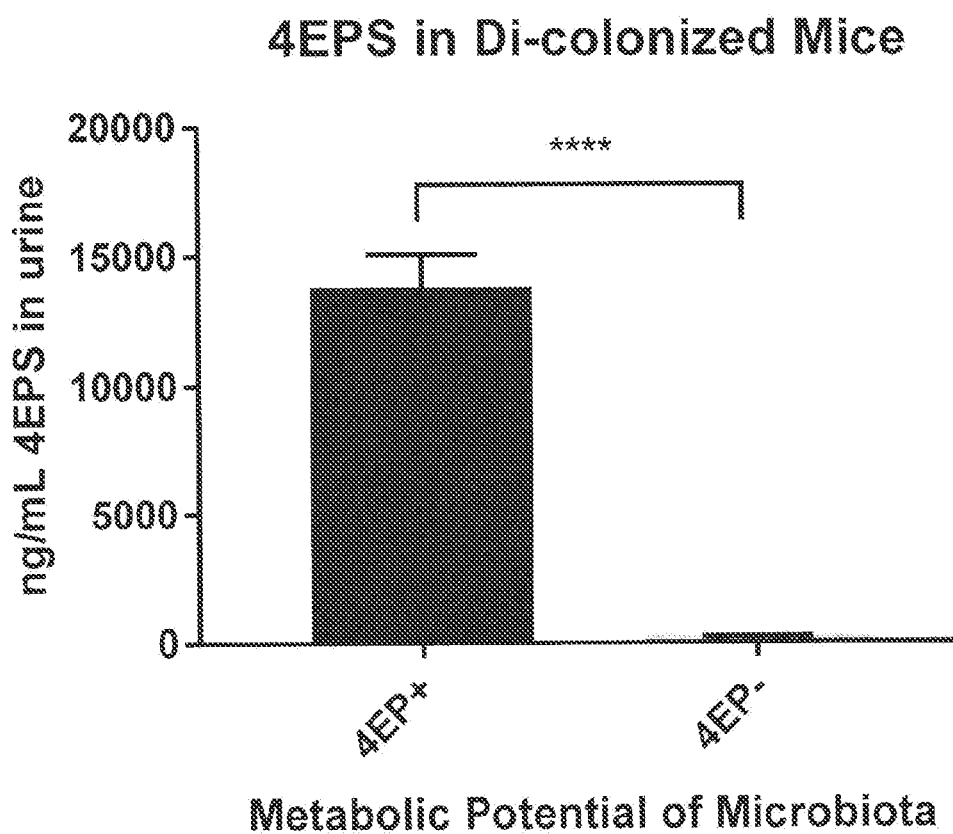
FIG. 1 shows urinary 4-EPS Levels in 4EP+ and 4EP− di-colonized mice. Germ-free wild-type C57BL/6 mice were di-colonized at 4 weeks of age by single oral gavage with either the B. ovatus and L. plantarum pair of strains that produces 4-EP or the pair that does not produce 4-EP. High 4-EPS production in vivo with colonization by the 4-EP producing pair (4EP+) and low 4-EPS production with colonization by the 4-EP non-producing pair (4EP−) were demonstrated via measurement of 4EPS levels in urine at age 5 weeks, prior to providing an AB-2004 preparation comprising AST-120.

Unusually high intestinal or systemic levels of certain microbial metabolites, as compared to healthy individuals, can be found in various central nervous system (CNS) diseases and disorders, such as autism spectrum disorder, schizophrenia, an anxiety disorder, depression, Parkinson's Disease, Rett Syndrome, Fragile X Syndrome, Tuberous Sclerosis, Multiple Sclerosis, Alzheimer's Disease, Angelman Syndrome, Williams Syndrome, amyotrophic lateral sclerosis, leukodystrophies including Alexander Syndrome, alpha-synucleinopathies including Lewy Body Dementia, incidental Lewy body disease, Lewy body variant of Alzheimer's disease, multiple system atrophy, and/or pure autonomic failure. Reduction of the levels of these microbial metabolites (and host-generated modifications of these metabolites) will lead to alleviation and/or reversal of behavioral and/or other neurological symptoms or conditions, as well as, neurological diseases. Without being bound to any theory, contemplated within the present disclosure are methods and compositions configured to or designed to lower the systemic levels of microbial metabolites (and host-generated modifications of these metabolites) to levels commensurate with (e.g., the same as or lower than) healthy individuals by administering or providing to a subject (e.g., a human, mammal or domestic animal) having such a central nervous system (CNS) disease or disorder associated with raised systemic levels of such microbial metabolites (and host-generated modifications of these metabolites), a non-absorbable composition, such as a polymer, clay, resin, carbon-based or other chemical moiety, which is capable of or configured to selectively bind microbial metabolites (and host-generated modifications of these metabolites) in the gut thereby alleviating, inhibiting, or mitigating absorption and/or transport of the microbial metabolites (and host-generated modifications of these metabolites) into peripheral tissues. The metabolite-laden composition will then be excreted from the subject in the feces, thereby permanently removing the microbial metabolites (and host-generated modifications of these metabolites) and improving said CNS symptoms, diseases and/or disorders in said subject. Certain microbial metabolites (e.g., 4-ethylphenol (4-EP) and p-cresol (PC)) have been identified as being correlated with and are believed to be causal of neurodevelopmental and behavioral disorders such as ASD. These metabolites may gain adventitious entry into systemic circulation through the "leaky gut" comorbidity often associated with such disorders. Once in systemic circulation these metabolites may act directly on relevant metabolic and signaling pathways to contribute to disease progression, systems and/or pathology. In addition, metabolites can be further metabolized by normal host processes to create new metabolites (e.g., 4-EPS and PCS) that can have adverse neurological effects, as well.

Thus, as disclosed in the experimental examples below, 4-EP over-producing mice were experimentally created by di-colonization for 3-5 weeks of germ-free mice with engineered *Bacteroides ovatus* and *Lactobacillus plantarum*. In standard mouse behavioral tests, these 4EP over-producing mice were shown to demonstrate ASD-associated behaviors and symptoms; and, further, it was shown that the administration of sequestering agents (e.g., AB-2004) that are capable of binding 4-EP and other metabolites in these mice can ameliorate such ASD-associated behaviors and symptoms. These results were surprising: a previous study had shown that 4-EPS (the host-sulfated version of 4-EP), when provided as a single bolus injection intraperitoneally, engendered symptoms of anxiety in naïve, wild-type mice but did not engender any core symptoms of autism spectrum disorder.

By sequestering these metabolites at the source of their production, e.g., in the gut of the subject, the translocation of the microbial metabolites (and host-generated modifications of these metabolites) into peripheral tissues will be minimized or eliminated. The net effect is the minimization of the impact of these metabolites and their further metabolites on the subject. Using a non-absorbable material, such as a biocompatible polymer or an activated carbon preparation such as an AB-2004 preparation, the target metabolites are permanently removed through normal passage through and excretion from the gut.

Some alternatives of the methods described herein comprise methods of treating, inhibiting, or ameliorating a neurological disorder associated with an alteration in the intestinal microbiome of a subject, such as a human, mammal, or domestic animal, wherein said methods comprise administering or providing to said subject a composition, which sequesters said microbial metabolites (and host-generated modifications of these metabolites), wherein said composition having sequestered intestinal metabolites is eliminated from the digestive tract without being metabolized. In some embodiments, the method further comprises the step of identifying and/or selecting a subject having elevated levels of one or more microbial metabolites (and host-generated modifications of these metabolites). According to some embodiments, the methods described herein may comprise methods of treating, inhibiting, or ameliorating leaky gut or leaky gut symptoms associated with said one or more neurological disorders. According to some embodiments, the methods described herein may comprise methods of treating, inhibiting, or ameliorating leaky gut or leaky gut symptoms not associated with said one or more neurological disorders. According to some embodiments, the methods described herein may comprise methods of treating, inhibiting, or ameliorating one or more neurological disorders independent of any effect on leaky gut or leaky gut symptoms.

For purposes of the present disclosure, the following definitions are provided.

As used herein, when referring to the term "intestinal dysbiosis" means an imbalance or maladaptation of the flora or microbiota within the gut or intestines, and particularly the small intestine. Such dysbiosis is characterized by a change in the composition of the intestinal or gut microbiome, in terms of the species/strains which are present and/or the relative abundance or proportion of the species/strains which are present, in which the change has a deleterious effect on the host organism. The deleterious effect on the host organism can result from microbiome-mediated changes in electrolyte balance, biofilm formation, integrity of the barrier formed by the intestinal epithelial lining, or the release from the microbiome of metabolites which are directly (e.g., as toxicity or effectors) or indirectly (e.g., as pre-cursors to toxins or effector) injurious to the health of the host.

As used herein, the term "intestinal hyperpermeability" means abnormal increased permeability of the barrier formed by the intestinal epithelial lining between the intestinal lumen and the surrounding issues. Such hyperpermeability may result from inflammation of the intestinal lining and/or failure of the tight junctions between cells of the intestinal epithelium, which allows the passage of substances from the lumen into the surrounding tissues where some may enter the peritoneal cavity and/or systemic circulation. Because of this leakage of substances from the gut or intestinal lumen, intestinal hyperpermeability may be referred to as "leaky gut" or "leaky gut syndrome."

As used herein with respect to sequestrant compositions, the term "biocompatible" means that the sequestrant composition does not have clinically significant toxic or injurious effects, locally or systemically. The term "biocompatible" does not exclude the possibility that a sequestrant composition may affect the passage of partially digested food (e.g., chyme, chyle, feces) through the intestines or induce some degree of diarrhea or constipation.

As used herein with respect to sequestrant compositions, the term "indigestible" means that the sequestrant composition is substantially resistant to degradation in the environment of the gastrointestinal tract such that at least 50%, and preferably more than 60%, 70%, 80% 90% or 95% of the sequestrant composition by weight is present in bulk (e.g., particulate, granular, fibrous) and not dissolved form when eliminated from the rectum.

As used herein with respect to sequestrant compositions, the term "non-absorbable" means that the sequestrant composition is substantially incapable of being absorbed by the lining of the gastrointestinal epithelium such that less than 25%, and preferably less than 20%, 15%, 10%, 5% or 1% of the sequestrant composition by weight is absorbed by the gastrointestinal epithelium.

As used herein with respect to metabolites and symptoms or disorders, the term "associated" means that the presence or level of a metabolite has been statistically significantly correlated (at least $p<0.05$, preferably $p<0.01$ or $p<0.001$) with the presence or degree of the symptom or disorder, and/or that the metabolite or a reaction product of the metabolite has been causally or mechanistically related to the development, maintenance or degree of the symptom or disorder.

As used herein, the term "autism spectrum disorder" or "ASD" means a neurological and developmental disorder that begins early in childhood and has a range of symptoms including: impaired social interactions; a disturbance in the comprehension of language; impaired and delayed verbal and written communication; restricted repetitive and stereotyped patterns of behavior, interests and activities; hyperactivity; short attention span; impulsivity; aggressiveness; self-injurious behaviors; and, particularly in young children, temper tantrums. ASD is now understood to include disorders previously identified as distinct: Autistic Disorder, Asperger's Disorder and Pervasive Developmental Disorder (Not Otherwise Specified). See, for example, *The Diagnostic and Statistical Manual of Mental Disorders*, Fourth Edition, Washington, D.C., American Psychiatric Association, 1994 ("DSM-IV"). Disorders related to ASD include Rett Syndrome and Childhood Disintegrative Disorder.

As used herein, the term "anxiety disorder" means a disorder characterized by an abnormal state of worry or fear, and includes subtypes such as acute stress disorder, generalized anxiety disorder, panic disorder, social anxiety disorder, agoraphobia, obsessive-compulsive disorder, post-traumatic stress disorder, selective mutism, or separation anxiety. Symptoms of anxiety vary depending on the type of anxiety experienced. The term "clinical anxiety" means an abnormally intense and disruptive level of anxiety, which is distinctly above normal levels of anxiety associated with a stressful situation. Clinical anxiety can be associated with any of the disorders listed above, or can be secondary to or symptomatic of another neurological disorder such as autism spectrum disorder (ASD) or schizophrenia. See, generally, DSM-IV, pages 393-444.

As used herein, the term "irritability" means an abnormally intense and disruptive level of irritability, including a tendency to be easily annoyed, upset or provoked to anger, which is distinctly above normal levels of irritability associated with an unpleasant or stressful situation. Clinical irritability can be associated with disorders including, without limitation, generalized anxiety disorder, autism spectrum disorders (ASD), post-traumatic stress disorder, attention-deficit disorder (ADD), attention-deficit hyperactivity disorder (ADHD), manic disorders, Alzheimer's Disease, borderline personality disorder, antisocial personality disorder, and schizoaffective disorder, or can be secondary to or symptomatic of another neurological disorder. Irritability can be measured clinically in humans using the Aberrant Behavior Checklist as described in Marcus et al. (2009), *J. Am. Acad. Child Adolesc. Psychiatry,* 48(11):1110-1119, and in Aman and Singh, *Aberrant Behavior Checklist: Manual.* East Aurora, N.Y.: Slos son Educational Publications; 1986.

"Subject" as used herein, refers to a human or a non-human mammal including but not limited to a dog, cat, horse, donkey, mule, cow, domestic buffalo, camel, llama, alpaca, bison, yak, goat, sheep, pig, elk, deer, domestic antelope, or a non-human primate selected or identified for removal of one or more microbial metabolites (and host-generated modifications of these metabolites) or selected or identified for treatment, inhibition, amelioration of a neurological disease or neurological disorder, or any symptom thereof, associated with an alteration in the intestinal microbiome, including without limitation autism spectrum disorder (ASD), schizophrenia, an anxiety disorder, depression, Parkinson's Disease, Fragile X, Rett Syndrome, Tuberous Sclerosis, leukodystrophies including Alexander Syndrome, alpha-synucleinopathies including Lewy Body Dementia, and/or Alzheimer's Disease.

"Subject suspected of having" refers to a subject exhibiting one or more clinical indicators of a disease or condition. In certain embodiments, the disease or condition may comprise one or more of autism spectrum disorder, an anxiety disorder, Fragile X, Rett syndrome, tuberous sclerosis, obsessive compulsive disorder, attention deficit disorder, and/or schizophrenia.

"Subject in need thereof" refers to a subject selected or identified as one being in need of a composition that removes or sequesters one or more microbial metabolites (and host-generated modifications of these metabolites) or one in need of a treatment, inhibition, amelioration of a neurological disease or neurological disorder associated with an alteration in the intestinal microbiome such as autism spectrum disorder, an anxiety disorder, Parkinson's Disease, Rett Syndrome, Fragile X Syndrome, Tuberous Sclerosis, Multiple Sclerosis, Alzheimer's Disease, Angelman Syndrome, Williams Syndrome, amyotrophic lateral sclerosis, leukodystrophies including Alexander Syndrome, alpha-synucleinopathies including Lewy Body Dementia, incidental Lewy body disease, Lewy body variant of Alzheimer's disease, multiple system atrophy, pure autonomic failure, or any combination thereof.

A "therapeutic effect" relieves or alleviates, to at least some extent, one or more of the symptoms of a disease or disorder, and includes curing the disease or disorder. "Curing" means that the symptoms of active disease are eliminated. However, certain long-term or permanent effects of the disease may exist even after a cure is obtained (such as tissue damage).

"Amelioration" refers to a lessening of severity of at least one indicator of a condition or disease. In certain embodiments, amelioration includes a delay or slowing in the progression of one or more indicators of a condition or disease. The severity of indicators can be determined by subjective or objective measures which are known to those skilled in the art.

"Modulation" refers to a perturbation of function or activity. In certain embodiments, modulation refers to an increase in gene expression. In certain embodiments, modulation refers to a decrease in gene expression. In certain embodiments, modulation refers to an increase or decrease in total serum levels of a specific protein. In certain embodiments, modulation refers to an increase or decrease in free serum levels of a specific protein. In certain embodiments, modulation refers to an increase or decrease in total serum levels of a specific non-protein factor, e.g., a metabolite. In certain embodiments, modulation refers to an increase or decrease in free serum levels of a specific non-protein factor. In certain embodiments, modulation refers to an increase or decrease in total bioavailability of a specific protein. In certain embodiments, modulation refers to an increase or decrease in total bioavailability of a specific non-protein factor.

"Lipid number" is an art-recognized term used to define the structural features of fatty acids and lipids. For example, in "docosapentaenoate (n3 DPA; 22:5n3)", "22" refers to the total number of carbons; "5" refers to the total number of unsaturated (double) bonds and "n3" refers to the position of the carbon atom where the first unsaturation occurs, as numbered from the end opposite of the carboxylate group.

Sequestrant Preparations

In some embodiments, the compositions to be administered according to the methods described herein may comprise, consist essentially of, or consist of one or more of an adsorbent, polymer, clay or resin, wherein said adsorbent, polymer, clay or resin may further comprise an activated carbon, an apatite or hydroxyapatite, a kaolin, a bentonite, a pectin, a cellulose polymer, an ion exchange resin, a cholestyramine polymer, a tetraethylenepentamine polymer, a phenolic resin, a boronic acid-presenting polymer, a catechin-presenting polymer, a zeolite, and/or a nanoparticle, or any combination thereof.

In some embodiments, according to the methods of the present disclosure, the sequestrant composition to be administered comprises, consists essentially of, or consists of a carbon material or activated carbon material. Said carbon materials or activated carbon materials have average particle sizes of 5-40 nm, 25-100 nm, 50-300 nm, 150-500 nm, 300 nm-1 µm, 0.5 µm-2 µm, 1 µm-5 µm, 2.5-10 µm, 6-20 µm, 15-50 µm, 30-100 µm, 75-150 µm, 100-300 µm, 250-500 µm, 300-750 µm, 600 µm-1 mm, or greater than 1 mm or a size that is within a range defined by any two of the aforementioned sizes. In some embodiments, said carbon materials or activated carbon materials have particle sizes of 300 µm-1 mm, 1-3 mm, 2-5 mm, or greater than 5 mm or a size that is within a range defined by any two of the aforementioned sizes. Said carbon materials or activated carbon materials also comprise a plurality of pores and a specific surface area in the range of from 20 $m^2/g$ to 5000 $m^2/g$, such as, e.g., 20, 50, 100, 250, 500, 750, 1000, 1500, 2000, 2500, 3000, 3500, 4000, 4500 or 5000 $m^2/g$ or a specific surface area within a range defined by any two of the aforementioned surface areas. Specific surface area can be determined using known methods, such as, for example, the method of Bruanauer, Emmett and Teller (*J. Am. Chem. Soc.* (1938), 60:309-311) and/or mercury porosimetry. See, e.g., ASTM Test Methods D3663, D6556, and D4567, each of which is incorporated by reference in its entirety.

Said carbon materials or activated carbon materials may additionally have a specific pore volume (determined on the basis of pores having a diameter of 1.7 nm to 100 nm) that is from 0.1 $cm^3/g$ to 1.5 $cm^3/g$, from 0.1 $cm^3/g$ to 0.8 $cm^3/g$, from 0.1 $cm^3/g$ to 0.7 $cm^3/g$, from 0.1 $cm^3/g$ to 0.6 $cm^3/g$, from 0.1 $cm^3/g$ to 0.5 $cm^3/g$, from 0.2 $cm^3/g$ to 0.8 $cm^3/g$, from 0.2 $cm^3/g$ to 0.7 $cm^3/g$, from 0.2 $cm^3/g$ to 0.6 $cm^3/g$, from 0.2 $cm^3/g$ to 0.5 $cm^3/g$, from 0.3 $cm^3/g$ to 1 $cm^3/g$, from 0.3 $cm^3/g$ to 0.9 $cm^3/g$, from 0.3 $cm^3/g$ to 0.8 $cm^3/g$, from 0.3 $cm^3/g$ to 0.7 $cm^3/g$, from 0.3 $cm^3/g$ to 0.6 $cm^3/g$, or from 0.3 $cm^3/g$ to 0.5 $cm^3/g$ or within a range defined by any two of the aforementioned values, as measured by a method for determining pore diameters and specific pore volumes, such as that described in Barrett, Joyner and Halenda (1951), *J. Am. Chem. Soc.* 73:373-380 and ASTM D4222-03 (2008) (the method referred to herein as the "BJH method"), both of which are expressly incorporated herein by reference in their entireties, and by the method of mercury porosimetry (e.g., using a mercury porosimeter, such as, for example, the Micromeritics Autopore V 9605 Mercury Porosimeter (Micromeritics Instrument Corp., Norcross, Ga.) in accordance with the manufacturer's instructions). See e.g., ASTM 3663, ASTM D-4284-12 and D6761-07 (2012), all of which are incorporated herein by reference. Said carbon material or activated carbon material may further have a mean pore diameter in the range of from 2 nm to 100 nm, as measured by the BJH method and/or mercury porosimetry. More typically, the carbon material or activated carbon material may have a mean pore diameter in the range of from 2-5 nm, from 3-9 nm, from 6-15 nm, from 10 nm to 90 nm or a size that is within a range defined by any two of the aforementioned sizes, as measured by the BJH method and/or mercury porosimetry. In some embodiments, the mean pore diameter is in the range of from 10 nm to 80 nm, or from 10 nm to 70 nm, or from 10 nm to 60 nm, and often from 10 nm to 50 nm or a size that is within a range defined by any two of the aforementioned sizes, as determined by the BJH method and/or mercury porosimetry. In some embodiments, the mean pore diameter is in the range of from 20 nm to 100 nm or a size that is within a range defined by any two of the aforementioned sizes, as measured by the BJH method and/or mercury porosimetry. In certain of these embodiments, the mean pore diameter is in the range from 20 nm to 90 nm, or from 20 nm to 80 nm, or from 20 nm to 70 nm, or from 20 nm to 60 nm, or from 10 nm to 50 nm or a size that is within a range defined by any two of the aforementioned sizes, as determined by the BJH method and/or mercury porosimetry.

In some embodiments, the methods of the present disclosure contemplate the administration of an adsorbent comprising an AB-2004 preparation. As used herein, the term "AB-2004" or "AB-2004 preparation" refers to a preparation of spherical activated carbon particles (a) having a minimum average specific surface area determined by the Brunauer-Emmett-Teller (BET) method of at least 500 $m^2/g$, at least 600 $m^2/g$, at least 700 $m^2/g$, or at least 800 $m^2/g$ and a maximum average specific surface area determined by the Brunauer-Emmett-Teller (BET) method less than 2000 $m^2/g$, less than 3000 $m^2/g$, or less than 4000 $m^2/g$, and/or a minimum average specific surface area determined by Langmuir's adsorption equation of at least 500 $m^2/g$, at least 1000 $m^2/g$ or at least 2000 $m^2/g$; and (b) having a minimum average particle diameter of at least 0.005, at least 0.01 mm, at least 0.05 mm, and a maximum average particle diameter of less than 1.5 mm, less than 1 mm, or less than 0.2 mm. In some embodiments, the AB-2004 preparation comprises activated charcoal particles comprising not less than 0.5 wt % nitrogen atoms. Said spherical activated carbon can be prepared using a thermoplastic resin, thermosetting resin, or ion exchange resin containing nitrogen atoms, as a carbon source; where said thermoplastic resin or ion exchange resin may contain a monomer selected from the group consisting of acrylonitrile, ethylacrylonitrile, methylacrylonitrile, diphenylacrylonitrile, and chloroacrylonitrile; and said thermosetting resin may contain a monomer selected from the group consisting of melamine and urea. Said spherical activated carbon may further be surface-unmodified, and may have a total acidic group content from 0.40 to 1.00 meq/g, less than 0.40 meq/g (but not zero), less than 0.30 meq/g (but not zero), and/or a total amount of basic groups from 0.40 to 1.10 meq/g. Alternatively, said spherical activated carbon can be surface modified, for example by oxidation, which can be performed in an atmosphere containing from 0.1 vol % to 50 vol % oxygen, from 1 vol % to 30 vol %, or from 3 vol % to 20 vol %; at a temperature from 300° C. to 800° C. or from 320° C. to 600° C. Said spherical activated carbon can be further modified, or may alternatively be surface modified by other procedures, for example by reduction, which can be performed at a temperature from 800° C. to 1200° C. or from 800° C. to 1000° C.

Exemplary carbon/activated carbon materials, also known as "activated charcoal," that are useful in the manufacture of non-absorbable spherical particle preparations, including AB-2004 preparations, are available from numerous manufacturers, including Kureha Corporation (Japan), Aditya Birla Group (India), Orion Engineered Carbons S.A. (Luxembourg), Asbury Graphite Mills, Inc. (Asbury, N.J.), Cabot Corporation (Boston, Mass.), Continental Carbon Company (Houston, Tex.), Sid Richardson Carbon & Energy Co. (Fort Worth, Tex.) and Imerys Graphite and Carbon (Switzerland). Various activated carbon/activated carbon products from these and other manufacturers can either be used in AB-2004 preparations, or can be adapted or modified for use in AB-2004 preparations.

Methods for producing a spherical activated carbon, including certain spherical activated carbon AB-2004 preparations of the invention, can be found in U.S. Pat. Nos. 9,877,987, 8,309,130, 7,651,974, 4,761,284 and 4,681,764, each of which is hereby expressly incorporated by reference in its entirety, and especially with respect to the disclosure of methods of making spherical activated carbon compositions and the spherical activated carbon compositions made thereby.

In some embodiments, according to the methods of the present disclosure, the sequestrant composition may comprise one or more of an apatite or hydroxyapatite. Said apatite or hydroxyapatite may have average particle sizes of 5-40 nm, 25-100 nm, 50-300 nm, 150-500 nm, 300 nm-1 µm, 0.5 µm-2 µm, 1 µm-5 µm, 2.5-10 µm, 6-20 µm, 15-50 µm, 30-100 µm, 75-150 µm, 100-300 µm, 250-500 µm, 300-750 µm, 600 µm-1 mm, or greater than 1 mm or a size that is within a range defined by any two of the aforementioned sizes. In some embodiments, said apatite or hydroxyapatite may have particle sizes of 300 µm-1 mm, 1-3 mm, 2-5 mm, or greater than 5 mm or a size that is within a range defined by any two of the aforementioned sizes. Said apatite or hydroxyapatite may also comprise a plurality of pores and a specific surface area in the range of from 20 m$^2$/g to 500 m$^2$/g, such as, e.g., 20, 30, 40, 50, 60, 70, 80, 90, 100, 120, 140, 160, 180, 200, 225, 250, 275, 300, 325, 350, 375, 400, 425, 450, 475, or 500 m$^2$/g or a specific surface area within a range defined by any two of the aforementioned surface areas. Specific surface area can be determined using known methods, such as, for example, the method of Bruanauer, Emmett and Teller and/or mercury porosimetry, as above.

An apatite or hydroxyapatite sequestrant may additionally have a specific pore volume (determined on the basis of pores having a diameter of 1.7 nm to 100 nm) that is from 0.1 cm$^3$/g to 1.5 cm$^3$/g, from 0.1 cm$^3$/g to 0.8 cm$^3$/g, from 0.1 cm$^3$/g to 0.7 cm$^3$/g, from 0.1 cm$^3$/g to 0.6 cm$^3$/g, from 0.1 cm$^3$/g to 0.5 cm$^3$/g, from 0.2 cm$^3$/g to 0.8 cm$^3$/g, from 0.2 cm$^3$/g to 0.7 cm$^3$/g, from 0.2 cm$^3$/g to 0.6 cm$^3$/g, from 0.2 cm$^3$/g to 0.5 cm$^3$/g, from 0.3 cm$^3$/g to 1 cm$^3$/g, from 0.3 cm$^3$/g to 0.9 cm$^3$/g, from 0.3 cm$^3$/g to 0.8 cm$^3$/g, from 0.3 cm$^3$/g to 0.7 cm$^3$/g, from 0.3 cm$^3$/g to 0.6 cm$^3$/g, or from 0.3 cm$^3$/g to 0.5 cm$^3$/g or within a range defined by any two of the aforementioned values, as measured by a method for determining pore diameters and specific pore volumes, such as the BJH method, or by mercury porosimetry, as above. Said apatite or hydroxyapatite sequestrants may further have a mean pore diameter in the range of from 10 nm to 100 nm, as measured by the BJH method and/or mercury porosimetry. More typically, the apatite or hydroxyapatite sequestrant may have a mean pore diameter in the range of from 2 nm to 90 nm, as measured by the BJH method and/or mercury porosimetry. In some embodiments, the mean pore diameter is in the range of from 2-5 nm, from 3-9 nm, from 6-15 nm, from 10 nm to 80 nm, or from 10 nm to 70 nm, or from 10 nm to 60 nm, and often from 10 nm to 50 nm or a size that is within a range defined by any two of the aforementioned sizes, as determined by the BJH method and/or mercury porosimetry. In some embodiments, the mean pore diameter is in the range of from 20 nm to 100 nm, as measured by the BJH method and/or mercury porosimetry. In certain of these embodiments, the mean pore diameter is in the range from 20 nm to 90 nm, or from 20 nm to 80 nm, or from 20 nm to 70 nm, or from 20 nm to 60 nm, or from 10 nm to 50 nm or a size that is within a range defined by any two of the aforementioned sizes, as determined by the BJH method and/or mercury porosimetry. Exemplary forms of apatite or hydroxyapatite sequestrants include milled particles, spray dried particles, spherical nanoparticles, and spherical microparticles.

In some embodiments according to the methods of the present disclosure, the sequestrant compositions may comprise, consist essentially of, or consist of one or more of an ingestible porous silica compound (e.g., calcium silica hydrate), such as the Micro-Cel E™ product (Imerys Graphite and Carbon, Bironico Switzerland). In some embodiments, according to the methods of the present disclosure, the sequestrant composition comprises an ingestible porous silica compound. Said ingestible porous silica compound may have average particle sizes of 5-40 nm, 25-100 nm, 50-300 nm, 150-500 nm, 300 nm-1 µm, 0.5 µm-2 µm, 1 µm-5 µm, 2.5-10 µm, 6-20 µm, 15-50 µm, 30-100 µm, 75-150 µm, 100-300 µm, 250-500 µm, 300-750 µm, 600 µm-1 mm, or greater than 1 mm or a size that is within a range defined by any two of the aforementioned sizes. In some embodiments, said ingestible porous silica compound may have particle sizes of 300 µm-1 mm, 1-3 mm, 2-5 mm, or greater than 5 mm or a size that is within a range defined by any two of the aforementioned sizes. Said ingestible porous silica compound may also comprise a plurality of pores and a specific surface area in the range of from 20 m$^2$/g to 500 m$^2$/g, such as, e.g., 20, 30, 40, 50, 60, 70, 80, 90, 100, 120, 140, 160, 180, 200, 225, 250, 275, 300, 325, 350, 375, 400, 425, 450, 475, or 500 m$^2$/g or a specific surface area within a range defined by any two of the aforementioned surface areas. Specific surface area can be determined using known methods, such as, for example, the method of Bruanauer, Emmett and Teller and/or mercury porosimetry, as above.

Said ingestible porous silica compound may additionally have a specific pore volume (determined on the basis of pores having a diameter of 1.7 nm to 100 nm) that is from 0.1 cm$^3$/g to 1.5 cm$^3$/g, from 0.1 cm$^3$/g to 0.8 cm$^3$/g, from 0.1 cm$^3$/g to 0.7 cm$^3$/g, from 0.1 cm$^3$/g to 0.6 cm$^3$/g, from 0.1 cm$^3$/g to 0.5 cm$^3$/g, from 0.2 cm$^3$/g to 0.8 cm$^3$/g, from 0.2 cm$^3$/g to 0.7 cm$^3$/g, from 0.2 cm$^3$/g to 0.6 cm$^3$/g, from 0.2 cm$^3$/g to 0.5 cm$^3$/g, from 0.3 cm$^3$/g to 1 cm$^3$/g, from 0.3 cm$^3$/g to 0.9 cm$^3$/g, from 0.3 cm$^3$/g to 0.8 cm$^3$/g, from 0.3 cm$^3$/g to 0.7 cm$^3$/g, from 0.3 cm$^3$/g to 0.6 cm$^3$/g, or from 0.3 cm³/g to 0.5 cm³/g or within a range defined by any two of the aforementioned values, as measured by a method for determining pore diameters and specific pore volumes, such as the BJH method, or by mercury porosimetry, as above. Said ingestible porous silica compound may further have a mean pore diameter in the range of from 2 nm to 100 nm, as measured by the BJH method and/or mercury porosimetry. More typically, the ingestible porous silica compound may have a mean pore diameter in the range of from 2 nm to 90 nm, as measured by the BJH method and/or mercury porosimetry. In some embodiments, the mean pore diameter is in the range of from 2-5 nm, from 3-9 nm, from 6-15 nm, from 10 nm to 80 nm, or from 10 nm to 70 nm, or from 10 nm to 60 nm, or from 10 nm to 50 nm or a size that is within a range defined by any two of the aforementioned sizes, as determined by the BJH method and/or mercury porosimetry. In some embodiments, the mean pore diameter is in the range of from 20 nm to 100 nm, as measured by the BJH method and/or mercury porosimetry. In certain of these embodiments, the mean pore diameter is in the range from 20 nm to 90 nm, or from 20 nm to 80 nm, or from 20 nm to 70 nm, or from 20 nm to 60 nm, or from 10 nm to 50 nm or a size that is within a range defined by any two of the aforementioned sizes, as determined by the BJH method and/or mercury porosimetry. Exemplary ingestible porous silica compounds are described in, for example, U.S. Pat. No. 6,666,214.

In some embodiments, according to the methods of the present disclosure, the sequestrant compositions may comprise one or more ingestible hydrocarbon or protein polymers. Exemplary ingestible polymers include but are not limited to guars, gums, chondroitin-based polymers, polyethylene-oxide polymers &, polyester, polylactic acid, polylactic-co-glycolic acid, cellulose, nitrocellulose, chitin, chitosan, polyethylene oxide, poly (β-benzyl-L-aspartate), poly (ε-caprolactone), polyglycolide, poly(DL-lactide-co-glycolide), polybutylcyanoacrylate, alginate, poly(adipic anhydride), 1,5-dioxepan-2-one, D,L-dilactide, polyvinyl acetate phthalate, methacrylic acid-methacrylic acid ester copolymers, trimellitate, poly(methacrylic acid), polyurethanes, polysiloxanes, polymethyl methacrylate, polyvinyl alcohol, polyethylene, polyvinyl pyrrolidone, epoxy resins, poly2-hydroxyethylmethacrylate, poly-N-vinyl pyrrolidone, polyvinyl alcohol, polyacrylic acid, polyacrylamide; polyethylene-co-vinyl acetate, polylactides, polyglycolides, polylactide-co-glycolides, polyanhydrides, and polyorthoesters and/or polyfluoroacrylic acid, or others as are known to those of skill in the art, or any combination thereof. These and many other pharmaceutically acceptable polymers are available from DowDuPont, Midland, Mich.

In some embodiments according to the methods of the present disclosure, the sequestrant compositions may comprise one or more of a cellulose polymer. Exemplary cellulose polymers include but are not limited to cellulose ethers, ethylcellulose, methylcellulose, hydroxyethylcellulose, hydroxymethylpropylcellulose, carboxymethylcellulose, carboxymethyl ethylcellulose, hydroxypropylcellulose, cellulose esters, cellulose acetate, cellulose acetate trimellitate, hydroxypropyl methyl cellulose phthalate, hydroxypropyl methylcellulose acetate succinate, cellulose acetate phthalate, and/or cellulose acetate propionate, or others as are known to those of skill in the art, and any combination thereof. Exemplary cellulose polymers may comprise cellulose acetate propionate having an average molecular weight of 10K, 25K, 50K, 100K, 150K, 200K, 250K, 500K, 750K, 1000K or more, or within a range defined by any two of the values disclosed herein, as determined by gel permeation chromatography.

In some embodiments according to the methods of the present disclosure, the compositions may comprise one or more of a weak base amine-containing resin and/or sepiolite. Exemplary amine containing resins include but are not limited to polyacrylamide, chitosan, amine-derivatized poly (methyl acrylate), epoxyamine resins, and/or any amine derivative of any polymer or resin otherwise disclosed herein, or any combination thereof.

In some embodiments according to the methods of the present disclosure, the sequestrant compositions may comprise, consist essentially of, or consist of one or more of an ion exchange resin. Exemplary ion exchange resins may comprise cellulose, polystyrene, acrylic ester, sulfonic acid polymer, sulfonic acid ester, polyethylenimine, polyamide, poly-styrene-divinylbenzene, or poly-phenol-formaldehyde, or other compounds. Commercially available ion exchange resins include but are not limited to Sepharose®, Sephadex®, Amberlite®, Amberlyst®, or Dowex®.

In some embodiments, the sequestrant composition may comprise a clay compound. In some embodiments, the compositions as described herein may comprise bentonite, alumina, or other clay compounds as are known in the art. In some embodiments, the compositions as disclosed herein may comprise a zeolite. In some further embodiments, said compositions may comprise clinoptilolite. In some embodiments, said clinoptilolite may have a general stoichiometry of $(Na,K,Ca)_{2-3}Al_3(Al,Si)_2Si_{13}O_{36} \cdot 12H_2O$.

It is understood by those of skill in the art that the resins, clays, polymers, cellulose derivatives, etc., disclosed herein or otherwise known in the art can be modified by conventional means such as by crosslinking or amination to be suitable for administration according to the methods of the present disclosure.

In some embodiments, the sequestrant composition can be administered multiple times. In some further embodiments, the same sequestrant composition is administered each time. In some further embodiments, the sequestrant composition to be administered in subsequent administrations can be different from that administered in the initial administration or in any previous administration. In some embodiments, further administrations can be employed at intervals as described herein, for such duration as is necessary to maintain reduced levels of intestinal metabolites relative to the levels identified prior to the first administration of the sequestrant composition.

In some embodiments according to the methods of the present disclosure, the sequestrant compositions and methods may further comprise a probiotic composition or administration of a probiotic composition, e.g., before, during, or after administration of the composition comprising, consisting essentially of, or consisting of the one or more sequestration agents. In some embodiments, the sequestrant compositions and or methods may comprise one or more of *Prevotella* species, *Bifido* bacteria species, *Parabacteriodes* species, (e.g., *P. merdae, P. distasonis*), *Faecalibacterium* species, (e.g., *F. prausnitzii*), *Eubacterium* species, *Coprococcus* species, *Lactobacillus reuteri, Lactobacillus rhamnosis, Bacteroides caccae, Bacteroides ovatus, Bacteroides fragilis, Bacteroides vulgatus*, and/or *Bacteroides thetaiotaomicron*, or any combination thereof, which can be administered before, during, or after administration of the composition comprising the one or more sequestration agents. In some embodiments, the methods of the present disclosure further comprise administration of a probiotic composition as a component of a sequestering composition. In some embodiments, the methods of the present disclosure further comprise administration of a probiotic composition in addition to a sequestering composition.

Formulations and Methods of Administration

"Administering" refers to providing a pharmaceutical agent, dietary supplement, or composition to a subject, and includes, but is not limited to, administering by a medical professional and self-administration. Administration of the compounds disclosed herein or the pharmaceutically acceptable salts thereof can be via any of the accepted modes of administration for agents that serve similar utilities including, but not limited to, orally, intraperitoneally, or rectally. Oral administrations are customary in administering the compositions that are the subject of the preferred embodiments. However in some embodiments, the compositions are administered rectally, such as by enema or suppository. In some embodiments, administration of the compounds may occur outside the body, for example, by apheresis or dialysis.

The term "agent" includes any substance, molecule, element, compound, entity, or a combination thereof. It includes, but is not limited to, e.g., protein, polypeptide, peptide or mimetic, small organic molecule, polysaccharide, polynucleotide, polymer, resin, organic or inorganic microparticle, organic or inorganic nanoparticle, and the like. It can be a natural product, a synthetic compound, or a chemical compound, or a combination of two or more substances.

The compounds useful as described above can be formulated into pharmaceutical compositions and/or dietary supplements for use in treating, inhibiting, or ameliorating a neurological disease or neurological disorder associated with an alteration in the intestinal microbiome such as autism Spectrum Disorder (ASD), schizophrenia, an anxiety disorder, depression, Parkinson's Disease, Fragile X, Rett Syndrome, Tuberous Sclerosis, leukodystrophies including Alexander Syndrome, alpha-synucleinopathies including Lewy Body Dementia, and/or Alzheimer's Disease. Standard pharmaceutical and/or dietary supplement formulation techniques are used, such as those disclosed in Remington's The Science and Practice of Pharmacy, 21st Ed., Lippincott Williams & Wilkins (2005), incorporated herein by reference in its entirety. Accordingly, some embodiments include pharmaceutical and/or dietary supplement compositions comprising, consisting essentially of, or consisting of: (a) a safe and therapeutically effective amount of one or more compounds described herein, or pharmaceutically acceptable salts thereof; and (b) a pharmaceutically acceptable carrier, diluent, excipient or combination thereof.

The term "pharmaceutically acceptable carrier" or "pharmaceutically acceptable excipient" includes any and all solvents, diluents, emulsifiers, binders, buffers, dispersion media, coatings, antibacterial and antifungal agents, isotonic and absorption delaying agents and the like, or any other such compound as is known by those of skill in the art to be useful in preparing pharmaceutical formulations. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art can be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the TWEENS; wetting agents, such as sodium lauryl sulfate; coloring agents; flavoring agents; tableting agents, stabilizers; antioxidants; preservatives; pyrogen-free water; isotonic saline; and/or phosphate buffer solutions, or any combination thereof.

The compositions described herein are preferably provided in unit dosage form. As used herein, a "unit dosage form" is a composition containing an amount of a compound that is suitable for administration to a subject, in a single dose, according to good medical practice. The preparation of a single or unit dosage form however, does not imply that the dosage form is administered once per day or once per course of therapy. A unit dosage form may comprise, consist essentially of, or consist of a single daily dose or a fractional sub-dose wherein several unit dosage forms are to be administered over the course of a day in order to complete a daily dose. According to the present disclosure, a unit dosage form can be given more or less often that once daily, and can be administered more than once during a course of therapy. Such dosage forms can be administered in any manner consistent with their formulation, including orally, rectally, nasally, and/or parenterally. While single administrations are specifically contemplated, the compositions administered according to the methods described herein may also be administered as a continuous infusion or via an implantable infusion pump.

The methods as described herein may utilize any of a variety of suitable forms for a variety of routes for administration, for example, for oral, nasal, or rectal routes of administration. Depending upon the particular route of administration desired, a variety of pharmaceutically-acceptable carriers well-known in the art can be used. Pharmaceutically-acceptable carriers include, for example, solid or liquid fillers, diluents, hydrotropes, surface-active agents, and encapsulating substances. Optional pharmaceutically-active materials can be included, which do not substantially interfere with the activity of the one or more compounds in the formulation. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and/or bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and/or melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and/or flavoring agents, or any combination thereof.

The pharmaceutically-acceptable carriers suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and/or cellulose; binders such as starch, gelatin and/or sucrose; disintegrants such as starch, alginic acid and/or croscarmelose; lubricants such as magnesium stearate, stearic acid, microcrystalline cellulose, carboxymethyl cellulose, and/or talc. Tablets may also comprise solubilizers or emulsifiers, such as poloxamers, cremophor/Kolliphor®/Lutrol®, or methylcellulose, hydroxypropylmethyl-cellulose, or others as are known in the art, or any combination thereof. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and/or fruit flavors, or any combination thereof, are useful adjuvants for chewable tablets. Capsules typically comprise one or more solid diluents disclosed above. The selection of carrier components depends on secondary considerations like taste, cost, and shelf stability, which can be readily made by a person skilled in the art.

Peroral (PO) compositions also include liquid solutions, emulsions, or suspensions. The pharmaceutically-acceptable carriers suitable for preparation of such compositions are well known in the art. Typical components of carriers for syrups, elixirs, emulsions and/or suspensions include ethanol, glycerol, propylene glycol, polyethylene glycol, liquid sucrose, sorbitol and/or water. For a suspension, typical suspending agents include methyl cellulose, sodium carboxymethyl cellulose, AVICEL RC-591, tragacanth and/or sodium alginate; typical wetting agents include lecithin and/or polysorbate 80; and typical preservatives include methyl paraben and/or sodium benzoate, or any combination thereof. Peroral liquid compositions may also contain one or more components such as sweeteners, flavoring agents and/or colorants, as disclosed above. Peroral compositions can also be in the form of foodstuffs, such as candy, an applesauce, a yogurt, a soft pudding, a gelatin foodstuff, a juice, milk, a soy or nut beverage, a thickened beverage, or a cheese, or any combination thereof.

Such compositions may also be coated by conventional methods, typically with pH or time-dependent coatings, such that the subject one or more compounds are released in the gastrointestinal tract in the vicinity of the desired application, or at various times to extend the desired action. Exemplary dosage forms for release in the gastrointestinal tract may incorporate one or more of cellulose acetate phthalate, polyvinyl acetate phthalate, hydroxypropyl methyl cellulose phthalate, ethyl cellulose, Eudragit coatings, waxes and/or shellac, or other excipients known to those of skill in the art, or any combination thereof. According to some embodiments, the compositions to be administered according to the methods described herein are formulated for release in the gastrointestinal tract. According to some embodiments, the compositions to be administered according to the methods described herein are formulated for release in the lower gastrointestinal tract. In some embodiments, the compositions are provided as enteric coated capsules, tablets, soft gels; or intrinsically enteric capsules.

The actual unit dose of the compositions described herein depends on the one or more compounds in the formulation. In some embodiments, the amount of each compound in the formulation can be from 5 mg/kg to 500 mg/kg or more of body weight per day, from 10 mg/kg or less to 70 mg/kg, from 50 mg/kg to 80 mg/kg of body weight per day, from 70 mg/kg to 120 mg/kg of body weight per day, from 100 mg/kg to 300 mg/kg of body weight per day, or from 250 mg/kg to 500 mg/kg of body weight per day. In some embodiments, the dose can be less than 100 mg/kg, 500 mg/kg, 300 mg/kg, 200 mg/kg, 150 mg/kg, 100 mg/kg, 50 mg/kg, 40 mg/kg, 30 mg/kg, 25 mg/kg, 20 mg/kg, 10 mg/kg, 7.5 mg/kg, 6 mg/kg, 5 mg/kg, 4 mg/kg, 3 mg/kg, 2.5 mg/kg, or 1 mg/kg of body weight per day or an amount that is within a range defined by any two of the aforementioned amounts. In some embodiments, the actual unit dose is 5, 10, 25, 50, 75, 100, 150, or 200 mg/kg of body weight per day or an amount that is within a range defined by any two of the aforementioned amounts. Thus, for administration to a 70 kg person, for example, the dosage range is from 350 mg to 750 mg, from 500 mg to 1 g, from 750 mg to 2 g, from 1 g to 5 g, from 2.5 g to 6 g, from 4 g to 10 g, from 8 g to 20 g, from 15 g to 35 g, or from 1 g or less to 35 g or more, or an amount that is within a range defined by any two of the aforementioned amounts. In some embodiments, the actual unit dose is 6 g. In some embodiments the actual unit dose is 10 g. In some embodiments, the actual unit dose is 35 g. In some embodiments, the actual unit dose is 1 g or less but not zero. In some embodiments, the actual unit dose is 10 g or less but not zero. In some embodiments, the actual unit dose is 35 mg or less but not zero.

"Loading dose," as used herein refers to an initial dose of a compound which is higher than subsequent doses.

"Maintenance dose," as used herein refers to a subsequent dose that follows a loading dose, and occurs later in time than a loading dose. One of ordinary skill in the art will be aware that the dosage form or mode of administration of a maintenance dose can be different from that used for the loading dose. In any of the embodiments disclosed herein, a maintenance dose may comprise administration of the unit dosage form on any dosing schedule contemplated herein, including but not limited to, monthly or multiple times per month, biweekly or multiple times each two weeks, weekly or multiple times per week, daily or multiple times per day. It is contemplated within the present disclosure that dosing holidays can be incorporated into the dosing period of the maintenance dose. Such dosing holidays may occur immediately after the administration of the loading dose or at any time during the period of administration of the maintenance dose. As used herein, the period of administration of the maintenance dose can be referred to as the "maintenance phase" of the treatment period.

"Mode of administration" as used herein refers to the avenue by which one or more compounds are administered to a subject. As used herein, "mode of administration" comprises the dosage form (for example, a tablet, powder, dissolved liquid, suspension, emulsion, etc.) and mechanism by which the dosage form is applied to the subject (for example, orally, such as by a pill, dissolved liquid, oral suspension). As used herein, "mode of administration" also comprises the dose, dose amount, and dosing schedule by which a compound is administered to a subject.

In some embodiments, the compositions to be administered according to the methods of the present disclosure are provided with, or mixed into, a foodstuff, beverage, or other ingestible item. In some embodiments, said beverage, foodstuff, or other ingestible item may comprise, consist essentially of, or consist of one or more of a candy, an applesauce, a yogurt, a soft pudding, a gelatin foodstuff, a juice, milk, a soy or nut beverage, a thickened beverage, or a cheese, or any combination thereof. One of ordinary skill will readily recognize that the combination of the compositions to be administered according to the methods of the disclosure can be combined with any suitable food or beverage to facilitate ingestion of the compositions.

Because levels of some metabolites will be expected to fluctuate in response to external stimuli, the methods according to the present disclosure contemplate varying or controlling the timing of administration of the compositions described herein, in order to enhance the effectiveness of the treatment, for example, by optimizing the removal of harmful metabolites or limiting the removal of helpful metabolites, in such a manner as to maintain both the somatic and the microbial health of the subject. In some embodiments, the compositions to be administered according to the methods of the present disclosure can be administered with food, such as concurrently with a meal or other ingestion of a foodstuff. In some further embodiments, the compositions to be administered according to the methods of the present disclosure can be administered immediately before or immediately after a meal or other ingestion of a foodstuff. In some further embodiments, the compositions to be administered according to the methods of the present disclosure can be administered within 1-5 minutes, within 3-10 minutes, within 6-15 minutes, within 10-20 minutes, within 15-30 minutes, within 20-45 minutes, or within one hour before or after a meal or other ingestion of a foodstuff. In some embodiments, the compositions to be administered according to the methods of the present disclosure can be administered without food, such as between 1-3 hours, between 2-5 hours, between 4-8 hours, between 6-12 hours, between 9-18 hours, between 12-24 hours, or more than 24 hours before or after a meal or other ingestion of a foodstuff.

As used herein, "duration of the treatment" refers to the time commencing with administration of the first dose and concluding with the administration of the final dose, such length of time being determined by one of ordinary skill in the art of treating neurological disorders or disorders implicating intestinal hyperpermeability (leaky gut), with reference to the symptoms and health of the subject being treated therefor. Such duration can be determined with reference to periodic, sporadic, or ongoing monitoring of the levels of the metabolites as disclosed herein or as known to one of skill in the art of treating neurological disorders and disorders implicating intestinal hyperpermeability (leaky gut).

As used herein, "dosing holiday" refers to a period of 24 hours or more during which either no dose is administered to the subject, or a reduced dose is administered to the subject. As used herein, "reduced dose" refers to a dose that is less than the total daily dose to be administered to a subject.

According to the methods disclosed herein, a reduction in serum metabolites is achieved by modulating the dosing schedule such that subjects experience periodic partial or full reductions in dosing for fixed amounts of time, followed by a resumption of dosing. In some embodiments, dosages are administered daily for between one and thirty days, followed by a dosing holiday lasting for between one and thirty days. In some embodiments, during the dosing holiday, no dose is administered. In some further embodiments, the composition of the present disclosure is allowed to clear completely from the subject's body prior to administration of the next dose. In some other embodiments, during the dosing holiday, a dose less than the usual daily dose is administered. In some further embodiments, an amount of the administered composition less than the therapeutically effective amount is allowed to remain within the subject during the dosing holiday. In some further embodiments, an amount of the administered composition sufficient to maintain therapeutic levels in the affected tissues is allowed to remain within the subject.

According to the present disclosure, the dosing schedule can be varied so as to attain the desired therapeutic effect. In each of the embodiments as disclosed herein, variations in dosing schedule can be repeated throughout the duration of the therapeutic protocol being administered. In each of the embodiments as disclosed herein, the first dosage can be higher, lower, or the same as the dosages following the first dosage. In each of the embodiments disclosed herein, a loading dose may precede the disclosed dosing regimen, and a dosing holiday may or may not follow the administration of the loading dose.

In some embodiments the methods of the present disclosure comprise administration of the one or more compositions provided herein daily or less frequently than daily, such as every second day, every third day, every fourth day, every fifth day, every sixth day, or every seventh day or for a time period that is within a range defined by any two of the aforementioned times.

The methods of the present disclosure can be used in the treatment, prevention, and/or amelioration of one or more neurological disorders including autism spectrum disorder, schizophrenia, an anxiety disorder, depression, Parkinson's Disease, Rett Syndrome, Fragile X Syndrome, Tuberous Sclerosis, Multiple Sclerosis, Alzheimer's Disease, Angelman Syndrome, Williams Syndrome, amyotrophic lateral sclerosis, leukodystrophies including Alexander Syndrome, alpha-synucleinopathies including Lewy Body Dementia, incidental Lewy body disease, Lewy body variant of Alzheimer's disease, multiple system atrophy, pure autonomic failure, or any combination thereof. Said disorders may include behavioral symptoms as are known in the art of clinical diagnosis and treatment of neurological disorders such as communicative symptoms, cognitive disorders, stereotyped behaviors, sensorimotor issues, clinical irritability, and/or anxiety-like behaviors in addition to physical symptoms as are known in the art of diagnosis and treatment of neurological disorders such as tremors, paralysis, dyskinesia, and/or gastrointestinal symptoms such as intestinal hyperpermeability (leaky gut). Accordingly, such clinical and/or diagnostic evaluations and determinations can be used to identify and/or select one or more subjects for receiving one or more compounds described herein in accordance with the one or more methods provided in this disclosure. The methods of the present disclosure may, in some embodiments, include monitoring of the behavioral, physical, and/or gastrointestinal symptoms as are known in the art of diagnosis and treatment of neurological disorders. In some embodiments, the methods according to the present disclosure incorporate monitoring changes in the behavior of a subject. In some further embodiments, the methods according to the present disclosure incorporate monitoring the subject for behavioral symptoms as are known to be related to autism spectrum disorder, schizophrenia, an anxiety disorder, depression, Parkinson's Disease, Rett Syndrome, Fragile X Syndrome, Tuberous Sclerosis, Multiple Sclerosis, Alzheimer's Disease, Angelman Syndrome, Williams Syndrome, amyotrophic lateral sclerosis, leukodystrophies including Alexander Syndrome, alpha-synucleinopathies including Lewy Body Dementia, incidental Lewy body disease, Lewy body variant of Alzheimer's disease, multiple system atrophy, pure autonomic failure, or any combination thereof. In some embodiments, the monitored behavioral symptoms do not comprise clinical anxiety. In some further embodiments, the methods according to the present disclosure incorporate monitoring the subject for repetitive behaviors, communicative symptoms, cognitive disorders, stereotyped behaviors, attachment to physical objects, aphasia, obsessive behaviors, unusual or inappropriate body language, gestures, and/or facial expressions and/or sensorimotor issues, lack of interest in other people, lack of empathy, difficulty grasping nonverbal cues, touch aversion, difficulty in socialization, speech delays, abnormal vocal tone or pitch, vocal repetition, perseveration, conversational difficulty, difficulty communicating needs or desires, inability to understand simple statements or questions, difficulties in processing language subtext, obsessive attachment to unusual objects, preoccupation, intolerance of changes in routine or environment, clumsiness, abnormal posture, odd ways of moving, fascination with particular objects, hyper- or hypo-reactivity to sensory input, clinical irritability or any combination thereof. Again, such clinical and/or diagnostic evaluations and determinations can be used to identify and/or select one or more subjects for receiving one or more compounds described herein in accordance with the one or more methods provided in this disclosure. In additional embodiments, the methods may incorporate monitoring the subject for tremors, paralysis, and/or dyskinesia, or other symptoms known to those in the art of diagnosing and treating neurological disorders, or any combination thereof. In some embodiments, the methods of the present disclosure may include monitoring of microbial and/or intestinal metabolites as disclosed herein or as known to those of skill in the art. According to the methods of the present disclosure, said metabolites can be monitored in the gut, feces, urine, blood, saliva, cerebrospinal fluid, and/or synovial fluid of a subject. The methods of the present disclosure contemplate the monitoring of said metabolites in any tissue or fluid obtainable from a subject during the course of treatment. Again, such clinical and/or diagnostic evaluations and determinations can be used to identify and/or select one or more subjects for receiving one or more compounds described herein in accordance with the one or more methods provided in this disclosure.

In some embodiments, the compositions are administered at any time following the onset of one or more of the aforementioned symptoms of a neurological disorder associated with intestinal hyperpermeability (leaky gut) and/or intestinal dysbiosis. In some embodiments, the compositions according to the methods described herein are administered prior to the onset of symptoms of said disorder or disorders. In some embodiments, the compositions according to the methods described herein are administered concurrently with or after the onset of symptoms of said disorder or disorders.

The methods described herein are further illustrated by the following examples.

Example 1

Establishment of 4EP-Producing Microbiota and Administration of AB-2004

The effect of 4EP production by the gastrointestinal microbiota was investigated using gnotobiotic mice that were di-colonized with strains engineered to differ solely in their capacity to produce 4EP, which is converted to 4EPS by the host. The effect of an AB-2004 preparation that sequesters 4-EP, its derivative 4-EPS and other toxic microbial metabolites, was investigated by formulating the AB-2004 into mouse food and administering it in parallel with a control diet that did not contain AB-2004 but was otherwise identical. Impact of 4EP production by the microbiota and AB-2004 administration was determined via assessments of repetitive, social and anxiety-like behaviors that represent core and non-core symptoms of autism spectrum disorders (ASD).

To produce the engineered strains, the *Bacteroides ovatus* gene for p-coumaric acid production was cloned in tandem with the *Bacillus subtilis* gene for phenolic acid decarboxylase into the *B. ovatus* chromosome to produce 4-vinylphenol. *Lactobacillus plantarum* converts 4-vinylphenol produced by the engineered *B. ovatus* strain to 4-EP. To produce a pair of otherwise identical strains that is incapable of 4EP production, a loss-of-function mutation was introduced into the *B. ovatus* strain, resulting in elimination of 4-vinylphenol production and consequently 4-EP production by *L. plantarum*.

Figure 2:
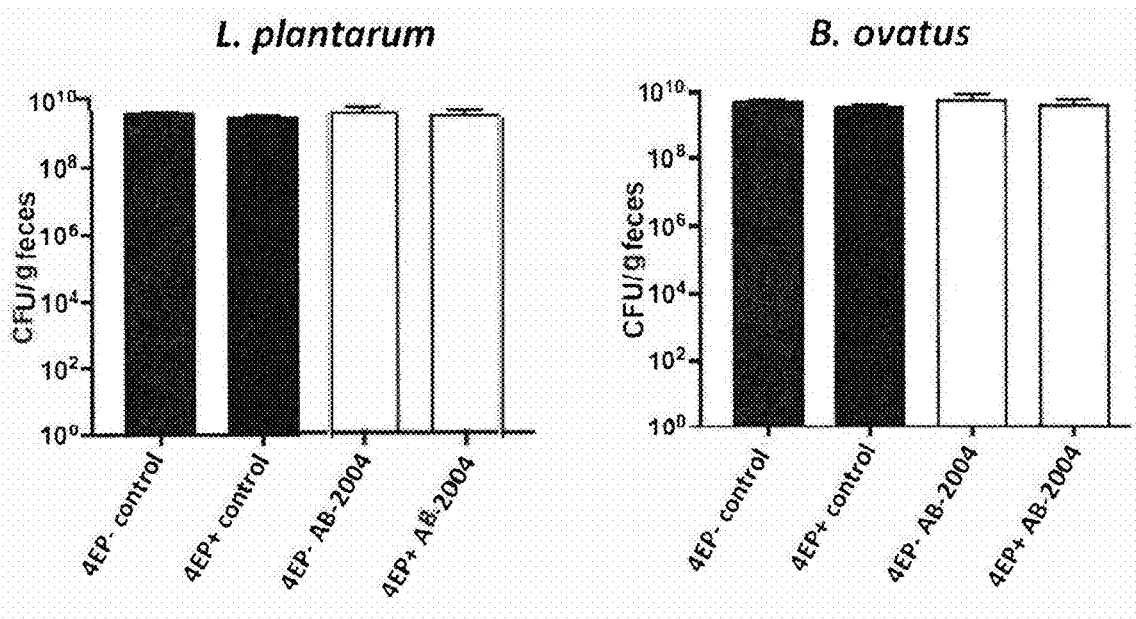
FIG. 2 shows that microbiota colonization levels are similar across groups. L. plantarum (left) and B. ovatus (right) achieved similar levels of colonization in mice regardless of whether they produced 4-EP and regardless of whether the mice were provided an AB-2004 preparation.

At the age of 5 weeks, mice were placed on a diet that contained 8% w/w of an AB-2004 preparation (AST-120, Kureha Corporation, Japan), or an otherwise identical diet that did not contain AB-2004. Colonization of mice was quantified by plating dilutions of fecal homogenates on solid media, and the two pairs of strains were confirmed to colonize mice to similar levels, as similar levels of colony forming units per mL fecal homogenate were produced in the assay (FIG. 2). Table 1 describes the identifiers used for groups of mice in figure labels in this section.

TABLE 1

Descriptions of Mouse Group Labels in Figures

| Mouse Group ID | Microbiota | Diet |
| --- | --- | --- |
| 4EP − Control | Does not produce 4EP | Control diet |
| 4EP + Control | Produces 4EP | Control diet |
| 4EP − AB-2004 | Does not produce 4EP | Contains 8% AB-2004 |
| 4EP + AB-2004 | Produces 4EP | Contains 8% AB-2004 |

Marble Burying

A marble burying test was used to assess repetitive behavior, which is a core symptom of ASD. In the assay as described by Malkova et al. (*Behav Immun.* 26(4):607-16 (2012)), marbles are placed on top of bedding in a cage, a test mouse is placed in the cage, and the number of marbles buried by the mouse during the test period is measured. As shown in FIG. 3(a), in the assay, mice on control diet that were di-colonized with 4-EP producing microbes buried significantly more marbles than mice on control diet that had been di-colonized with microbes that did not produce 4-EP, thereby demonstrating repetitive behavior due to 4EP production by the gut microbiota. Administration of AB-2004 normalized this repetitive behavior in the assay: mice with 4-EP producing microbiota on the AB-2004 diet burying significantly fewer marbles than mice with 4-EP producing microbiota on control diet. The data indicate that administration of materials that sequester 4-EP, 4-EPS and/or other toxic microbial metabolites can be beneficial for reducing repetitive behaviors, one of the core symptoms of ASD.

Elevated Plus Maze

The elevated plus maze (EPM) test of exploratory behavior was used to assess general locomotion and anxiety-like behavior. Mice were allowed 5 minutes to explore an elevated plus maze comprised of two open arms and two closed arms that extend from a common central platform. A small raised lip around the edges of the open arms helped prevent mice from slipping off. An overhead video camera was used to record the session, and Ethovision software (Noldus Information Technology, Sacramento, Calif.) was used to analyze mouse movements. Time spent in closed, relatively protected portions of the maze versus time spent exploring open, relatively exposed portions of the maze is interpreted as a measurement of anxiety. As shown in FIG. 3(b), in the assay, mice with 4-EP producing microbiota on control diet spent less time than mice on control diet with microbiota that does not produce 4-EP in open portions of the EPM versus closed portions of the EPM, thereby demonstrating anxiety-like behavior due to production of 4EP by the intestinal microbiota. Administration of an AB-2004 preparation normalized these anxiety-like behaviors in the assay, as mice with 4-EP producing microbiota on AB-2004 diet spent significantly more time in open versus closed portions of the EPM than mice with 4-EP producing microbiota mice on control diet that lacks AB-2004. Anxiety is a common non-core symptom of ASD, and these indicate that administration of sequestrants of 4-EP, 4-EPS and/or other toxic microbial metabolites can be beneficial in reducing anxiety symptoms in some ASD patients.

Open Field

Figure 4A:
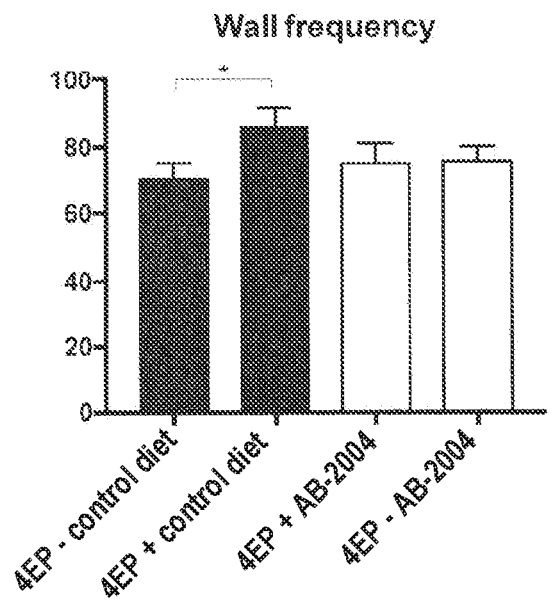
FIGS. 4A-4C show the results of an Open Field Test.
Figure 4B:
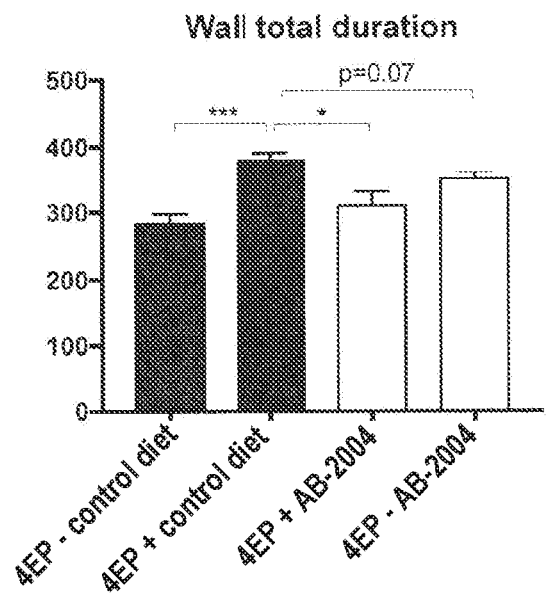
Figure 4C:
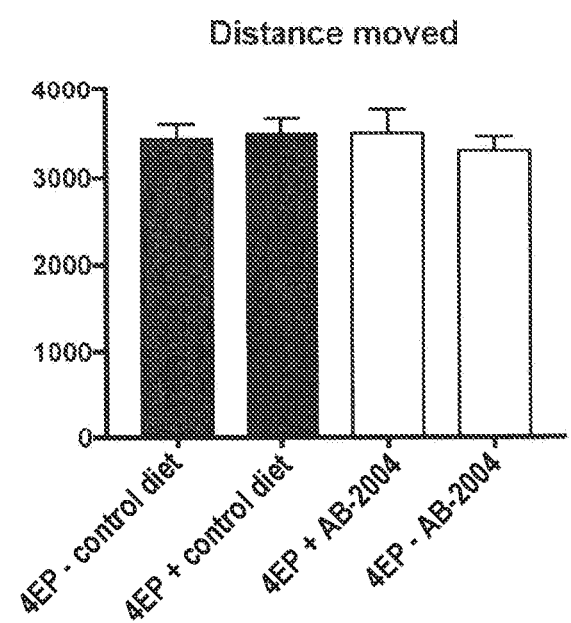

The open field test of exploratory behavior was used to assess general locomotion and anxiety-like behavior. For open-field testing, mice were allowed to explore a 50×50-cm white Plexiglas box for 10 min. An overhead video camera was used to record the session, and Ethovision software (Noldus Information Technology, Sacramento, Calif.) was used to analyze the distance traveled, and the number of entries and duration of time spent in the center arena (central square, 17×17 cm) versus the wall area of the box. Mice on control diet that had been colonized with 4-EP producing microbiota exhibited an anxiety-like phenotype in the assay, entering the wall area with greater frequency and spending more time in the wall area compared to mice on the control diet that had been colonized with microbiota that did not produce 4-EP. In the assay, the amount of time that mice that had been colonized with 4-EP producing microbiota on AB-2004 diet spent in the wall area (FIG. 4(B)) and the frequency with which they entered the wall area (FIG. 4(A)) were similar to mice that had been colonized with microbiota that do not produce 4-EP, suggesting normalization of this behavior by AB-2004. Total distance moved (FIG. 4(C)) in the open field test was similar for all groups, suggesting that differences in exploration of open versus closed parts of the field are not due to differences in the distance that the mice moved during the test. Consistent with the EPM data, these data provide additional evidence that administration of materials that sequester 4-EP, its derivative 4-EPS and/or other toxic microbial metabolites can be beneficial in alleviating symptoms of anxiety in ASD patients who suffer from them.

Direct Social Interaction

A three-chambered social approach test was used to measure direct social interaction. The test mouse was placed in the center chamber of three adjacent chambers, with a novel object in an adjacent terminal chamber and an unfamiliar mouse in the other adjacent terminal chamber. The test mouse was habituated in the apparatus for 10 minutes prior to initiation of scoring. The test mouse was able to pass through openings from the center chamber into each of the adjacent chambers. The test was recorded by video, and the time spent by the test mouse in the chamber with the unfamiliar mouse was scored manually. A higher amount of time spent with the unfamiliar mouse is an indicator of increased sociability, while a lower amount of time spent with the unfamiliar mouse is an indicator of decreased sociability, consistent with the social deficits that are a core symptom of Autism Spectrum Disorders.

Figure 5A:
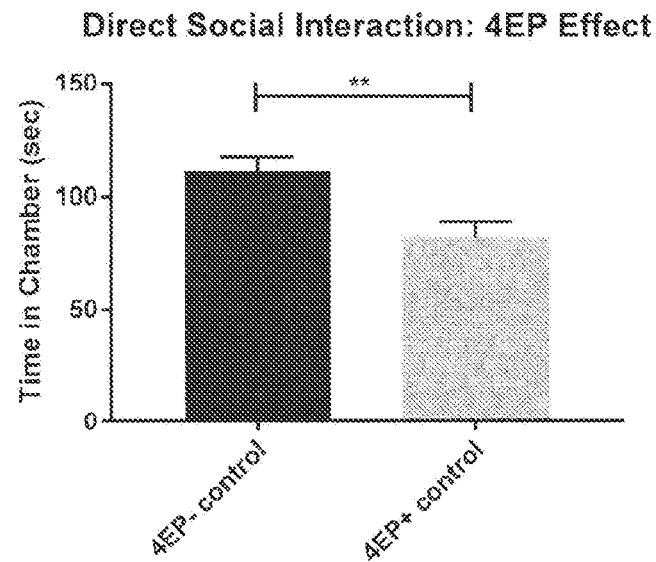
Figure 5B:
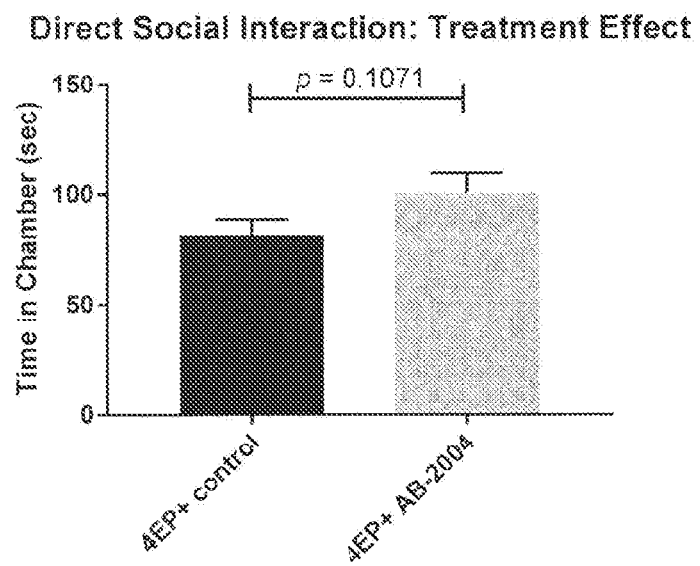

As shown in FIG. 5, in the three-chamber test of social interaction, male mice di-colonized with 4EP-producing microbiota spent significantly less time in the chamber with another mouse than male mice di-colonized with microbes that do not produce 4EP. In the assay, there was a trend for improvement of this social deficit by treatment with an AB-2004 preparation (p=0.1071). These data indicate that administration of materials such as AB-2004 that sequester 4EP, its derivative, 4EPS, and other toxic microbially-derived metabolites to patients with ASD can be beneficial to improve core symptoms of ASD, such as social deficits.

Example 2

Removal of Microbial Metabolites by Sequestrant Materials

A 50 mg/mL stock solution of a single microbial metabolite was prepared in dimethylsulfoxide (DMSO) and serially diluted (2:1) in DMSO to create standard solutions of 50, 25, 12.5, 6.25, 3.125, 1.56 and 0.78 mg/mL. Each DMSO standard solution (10 µL) was diluted into deionized water (990 µL) to create standard calibration samples of 0.5, 0.25, 0.125, 0.06, 0.03, 0.015, 0.078 mg/mL aqueous solutions (1% DMSO). A blank sample was prepared by adding 100 µL DMSO to 990 µL distilled water and the UV-absorbance of each aqueous standard solution was measured at a single wavelength using a Thermo Scientific NanoDrop™ spectrophotometer to identify the linear range of absorbance and generate a calibration curve.

A 0.5 mg/mL solution of a single microbial metabolite was prepared in deionized water by adding 100 µL of 50 mg/mL DMSO stock solution to 9.9 mL deionized water. Next, 50 mg/mL of one of a series of sequestrant material being tested was added and the solution was stirred at room temperature. The resulting mixture was sampled over a time course from 0 to <4 hours. At each time point, approximately 1 mL of sequestrant mixture was taken up by syringe and passed through a nylon syringe filter (0.2 µm). Each sample was appropriately diluted with deionized water and either transferred to a cuvette for analysis using a Thermo Scientific™ NanoDrop (Fisher Scientific, Waltham, Mass.) or transferred to a 96-well clear bottom plate for analysis using a Spectramax i3x (Molecular Devices, San Jose, Calif.).

The absorbance of 4-EP by various representative sequestrant materials was conducted according to the general protocol. The UV-absorbance of each sample was measured at 270 nm by spectrophotometry. The % remaining of 4-EP following treatment with representative adsorbent materials at 50 mg/mL for 2 hours is reported in Table 2.

The following meanings apply: "++++" refers to <10% remaining; "+++" refers to 10-30% remaining; "++" refers to 31-70% remaining; "+" refers to 71-90% remaining; NA refers >90% remaining or no absorption observed. The zeolite used was clinoptilolite, with the general stoichiometry of $(Na,K,Ca)_{2-3}Al_3(Al,Si)_2Si_{13}O_{36} \cdot 12H_2O$; bentonite preparation was produced from Bentonite B.P. (Halewood Chemicals, UK); activated charcoal preparation was produced from 260 mg Activated Charcoal Dietary Supplement capsules (Nature's Way, Green Bay, Wis.), and the AB-2004 preparation was produced from AST-120 (Kureha Corporation, Japan).

TABLE 2

Absorption of 4-EP

| Material | % Remaining | % remaining |
|---|---|---|
| zeolite | + | 84% |
| bentonite | +++ | 28% |
| cellulose acetate propionate $M_n$~15,000 | +++ | 17% |
| cellulose acetate propionate $M_n$~75,000 | +++ | 20% |
| AB-2004 | ++++ | <1% |
| Activated charcoal | ++++ | <1% |

Example 3

The removal of 4-EPS from test solutions by various representative sequestrant materials was conducted according to the general protocol given in Example 2 with the UV-absorbance of each sample measured at 265 nm using spectrophotometry. The % remaining of 4-EPS following provision of representative adsorbent materials at 50 mg/mL for 2 hours is reported in Table 3.

TABLE 3

Absorption of 4-ethylphenyl sulfate

| Material | % Remaining @ 2 hours | % remaining |
|---|---|---|
| zeolite | NA | 100% |
| bentonite | NA | 100% |
| cellulose acetate propionate $M_n$~75,000 | + | 85% |
| AB-2004 | ++++ | 1% |
| Activated charcoal | ++++ | <1% |

Example 4

The removal of p-cresol from test solutions by various representative sequestrant materials was conducted according to the general protocol given in Example 2 with the UV-absorbance of each sample measured at 260 nm using spectrophotometry. The % remaining of p-cresol following provision of representative adsorbent materials at 50 mg/mL for 2 hours is reported in Table 4.

TABLE 4

Absorption of p-cresol

| Material | % Remaining @ 2 hours | % remaining |
|---|---|---|
| zeolite | + | 78% |
| bentonite | ++ | 56% |
| cellulose acetate propionate $M_n$~75,000 | +++ | 28% |
| AB-2004 | ++++ | <1% |

Example 5

The removal of p-cresyl sulfate from test solutions by various representative sequestrant materials was conducted according to the general protocol given in Example 2 with the UV-absorbance of each sample measured at 260 nm using spectrophotometry. The % remaining of p-cresyl sulfate following treatment with representative adsorbent materials at 50 mg/mL for 2 hours is reported in Table 5.

TABLE 5

Absorption of p-cresyl sulfate

| Material | % Remaining @ 2 hours | % remaining |
|---|---|---|
| zeolite | NA | 91% |
| cellulose acetate propionate $M_n$~75,000 | NA | 88% |
| AB-2004 | ++++ | 2% |

Example 6

The removal of indole from test solutions by various representative sequestrant materials was conducted according to the general protocol given in Example 2 with the UV-absorbance of each sample measured at 278 nm using spectrophotometry. The % remaining of indole following provision of representative adsorbent materials at 50 mg/mL for 2 hours is reported in Table 6.

TABLE 6

Absorption of indole

| Material | % Remaining @ 2 hours | % remaining |
|---|---|---|
| Zeolite | ++ | 44% |
| Bentonite | +++ | 14% |
| cellulose acetate propionate $M_n$~75,000 | +++ | 13% |
| AB-2004 | ++++ | <1% |

Example 7

The removal of 3-indoxyl sulfate from test solutions by various representative sequestrant materials was conducted according to the general protocol given in Example 2 with the UV-absorbance of each sample measured at 260 nm using spectrophotometry. The % remaining of 3-indoxyl sulfate following treatment with representative adsorbent materials at 50 mg/mL for 2 hours is reported in Table 7.

TABLE 7

Absorption of 3-indoxyl sulfate

| Material | % Remaining @ 2 hours | % remaining |
|---|---|---|
| Zeolite | NA | 100% |
| Bentonite | NA | 100% |
| cellulose acetate propionate $M_n$~75,000 | + | 73% |
| AB-2004 | ++++ | 3% |

Example 8

The removal of 4-hydroxyphenylacetic acid from test solutions by various representative sequestrant materials was conducted according to the general protocol given in Example 2 with the UV-absorbance of each sample measured at 278 nm using spectrophotometry. The % remaining of tyrosine following treatment with representative adsorbent materials at 50 mg/mL for 2 hours is reported in Table 8.

TABLE 8

Absorption of 4-hydroxyphenylacetic acid

| Material | % Remaining @ 2 hours | % remaining |
|---|---|---|
| Zeolite | NA | 100% |
| Bentonite | NA | 100% |
| cellulose acetate propionate $M_n$~75,000 | + | 86% |
| AB-2004 | ++++ | <1% |

Example 9

The removal of 2-hydroxy-2(4-hydroxyphenyl)acetic acid from test solutions by various representative sequestrant materials was conducted according to the general protocol given in Example 2 with the UV-absorbance of each sample measured at 278 nm using spectrophotometry. The % remaining of 2-hydroxy-2(4-hydroxyphenyl)acetic acid following treatment with representative adsorbent materials at 50 mg/mL for 2 hours is reported in Table 9.

TABLE 9

Absorption of 2-hydroxy-2(4-hydroxyphenyl)acetic acid

| Material | % Remaining @ 2 hours | % remaining |
|---|---|---|
| Zeolite | NA | 100% |
| bentonite | NA | 100% |
| cellulose acetate propionate $M_n$~75,000 | + | 86% |
| AB-2004 | ++++ | <1% |

Example 10

The removal of L-homocitrulline from test solutions by various representative sequestrant materials was conducted according to the general protocol given in Example 2 with the UV-absorbance of each sample measured at 274 nm using spectrophotometry. The % remaining of L-homocitrulline following treatment with representative adsorbent materials at 50 mg/mL for 2 hours is reported in Table 10.

TABLE 10

Absorption of L-homocitrulline

| Material | % Remaining @ 2 hours | % remaining |
|---|---|---|
| Zeolite | NA | 90% |
| bentonite | NA | 91% |
| cellulose acetate propionate $M_n$~75,000 | NA | 94% |
| AB-2004 | ++++ | <1% |

Example 11

Indoxyl sulfate, p-cresyl sulfate, and 4-ethylphenyl sulfate, respectively, were separately dissolved in phosphate buffer at pH 6.8 and exposed to AB-2004 with stirring for various lengths of time. At various time points, samples were withdrawn and assayed for the presence of the respective compound (labeled "toxins" below), and the amount of each compound removed from solution was calculated. Results are shown below in Table 11, where "Activated Charcoal" refers to an AB-2004 preparation.

TABLE 11

| Stirring Time | Name | Amount of Toxin added, mg | Amount of Toxin found, mg | Activated Charcoal, g | Amount of Toxin Absorbed, mg/g |
|---|---|---|---|---|---|
| 4 hrs | Indoxyl Sulfate | 10.40 | 0.01 | 0.05091 | 204.1 |
|  | p-Cresol Sulfate | 9.90 | 1.70 | 0.06168 | 132.9 |
|  | 4-Ethylphenyl Sulfate | 10.00 | 0.44 | 0.05210 | 183.5 |
| 18 hrs | Indoxyl Sulfate | 10.44 | 0.53 | 0.05313 | 186.5 |
|  | p-Cresol Sulfate | 9.97 | 0.15 | 0.05871 | 167.3 |
|  | 4-Ethylphenyl Sulfate | 9.98 | 0.68 | 0.05311 | 175.1 |

These results indicate that maximal absorption occurs in less than four hours of exposure for each compound when exposed to an AB-2004 preparation.

Example 12

Indoxyl sulfate, p-cresyl sulfate, and 4-EP, were simultaneously dissolved in phosphate buffer at pH 6.8 to create a simulated metabolite mixture and exposed to AB-2004 with stirring for various lengths of time. At various time points, samples were withdrawn and assayed for the presence of the respective compound (labeled "toxins" below), and the amount of each compound removed from solution was calculated. Results are shown below in Table 12, where "Activated Charcoal" refers to an AB-2004 preparation.

TABLE 12

| Stirring Time | Name | Amount of Toxin added, mg | Amount of Toxin found, mg | Activated Charcoal, g | Amount of Toxin Absorbed, mg/g |
|---|---|---|---|---|---|
| 1 hrs | Indoxyl Sulfate | 10.72 | 2.70 | 0.05000 | 160.4 |
|  | p-Cresol Sulfate | 10.40 | 7.05 | 0.05000 | 67.0 |
|  | 4-Ethylphenyl Sulfate | 9.98 | 4.39 | 0.05000 | 111.8 |
| 2 hrs | Indoxyl Sulfate | 10.72 | 2.17 | 0.05500 | 155.5 |
|  | p-Cresol Sulfate | 10.40 | 6.90 | 0.05500 | 63.6 |
|  | 4-Ethylphenyl Sulfate | 9.98 | 3.98 | 0.05500 | 109.1 |
| 4 hrs | Indoxyl Sulfate | 10.72 | 2.30 | 0.05360 | 157.1 |
|  | p-Cresol Sulfate | 10.40 | 7.27 | 0.05360 | 58.4 |
|  | 4-Ethylphenyl Sulfate | 9.98 | 4.36 | 0.05360 | 104.9 |

These results indicate that maximal absorption occurs in less than four hours of exposure even for compounds in mixed solutions when exposed to an AB-2004 preparation.

Example 13

Figure 6:
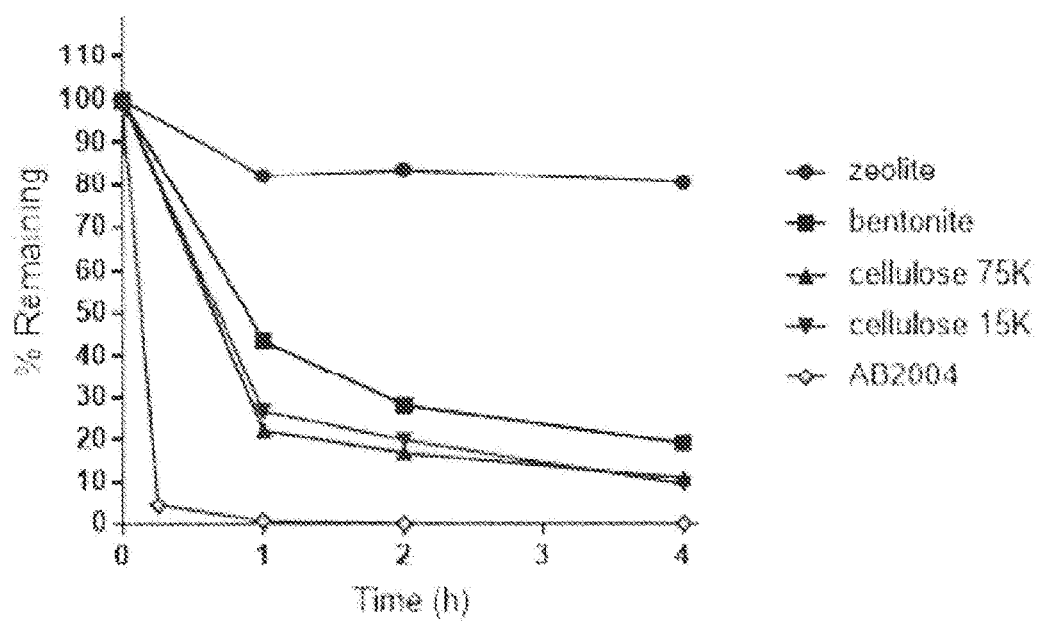
FIG. 6 shows a time course for adsorption of 4-EP by the sequestrants zeolite, bentonite, cellulose (75K), cellulose (15K), and an AB-2004 preparation. At a 1-hour timepoint, the AB-2004 preparation and the cellulose polymers both display >90% sequestration of 4-EP.

4-ethylphenyl sulfate, was dissolved in phosphate buffer at pH 6.8 and exposed to AB-2004, cellulose acetate propionate (MW 15K and 75K), bentonite, and clinoptilolite zeolite with stirring for various lengths of time. At various time points, samples were withdrawn and assayed for the presence of the respective compound, and the percentage of each compound removed from solution was calculated. Results are shown in FIG. 6.

These results provide evidence that cellulose based polymeric materials are effective sequestrants of the metabolite 4-EP.

Example 14

Removal of Microbial Metabolites in Fecal Slurry Supernatant by Sequestrant

To determine the capacity of AB-2004, bentonite, zeolite, cellulose acetate propionate (Mn ~15,000) and activated charcoal to adsorb the toxins 4-ethylphenol, p-cresol and 3-indoxyl sulfate from a complex mixture of metabolites similar to those found in the lumen of the human colon, an ex vivo assay was performed using human stool. A freshly collected stool was maintained at or below 4° C. In an anaerobic chamber (AS-580, Anaerobe Systems, Morgan Hill, Calif.) with an atmosphere of 5% carbon dioxide, 5% hydrogen and balance nitrogen, the stool was suspended in ice-cold phosphate buffered saline by pipetting to achieve 20% w/v fecal slurry, solids were allowed to settle, and the supernatant was transferred to conical tubes on ice prior to transfer to an aerobic atmosphere and −80° C. All subsequent steps were performed aerobically. Frozen aliquots were thawed on ice, centrifuged at 21,000×g for 3 minutes, and supernatant was transferred to fresh tubes and diluted with an equal volume of ice cold phosphate buffered saline. 4-ethylphenol, p-cresol and 3-indoxyl sulfate were prepared in dimethyl sulfoxide at 25 mg/mL and added to separate aliquots of the fecal slurry supernatant to a final concentration of 2 mg/mL. Spiked fecal slurry supernatants were added to the sequestrant materials consisting of an AB-2004 preparation, bentonite, zeolite, cellulose acetate propionate (Mn-15,000) and activated charcoal for 35-59 mg/mL final of the sequestrant materials, with the exception that activated charcoal was tested at 98 mg/mL versus p-cresol. The mixtures were incubated with vigorous mixing in conical tubes at 750 rpm at 10° C. for 4 hours and centrifuged at 21,000×g for 3 minutes. The supernatant was transferred to a 96-well plate and diluted 10-fold in phosphate buffered saline prior to determining the concentration of the metabolites by measuring absorption at 278 nm with a spectrophotometer (Spectramax i3x, Molecular Devices, San Jose, Calif.).

A standard curve was generated for each of the toxins by adding them to the fecal slurry supernatant at 4, 2, 1, 0.5 and 0.25 mg/mL final, diluting them 10-fold in phosphate buffered saline, and measuring absorption at 278 nm. The concentration of spiked 4-ethylphenol, p-cresol and 3-indoxyl sulfate in samples was determined by interpolation from the standard curves using GraphPad Prism 7 (GraphPad, La Jolla, Calif.). The percentage of spiked toxin that was removed by sequestrant was calculated by dividing the interpolated value by the interpolated value of a spiked control sample that was not treated with a sequestrant material and multiplying by 100. The percentage of spiked toxin removed by each sequestrant is shown in Table 13.

TABLE 13

Percentage Spiked Toxin Remaining in fecal slurry supernatant after 4 hours incubation with the indicated concentration of absorbent material.

| | Material | AB-2004 | Bentonite | Zeolite | Cellulose Acetate Propionate $M_n$~15,000 | Activated Charcoal |
|---|---|---|---|---|---|---|
| 4-Ethylphenol | % Remaining Range | ++++ | ++ | + | +++ | ++++ |
| | % Remaining | <1% | 52% | 88% | 27% | <1% |
| | Material Test Conc. (mg/mL) | 43.2 | 51.85 | 44.55 | 55.1 | 50.5 |

TABLE 13-continued

Percentage Spiked Toxin Remaining in fecal slurry supernatant after 4 hours incubation with the indicated concentration of absorbent material.

| | Material | AB-2004 | Bentonite | Zeolite | Cellulose Acetate Propionate $M_n$~15,000 | Activated Charcoal |
|---|---|---|---|---|---|---|
| Indoxyl Sulfate | % Remaining Range | ++++ | – | – | – | ++++ |
| | % Remaining | <1% | 95% | >99% | >99% | <1% |
| | Material Test Conc. (mg/mL) | 48.2 | 41.1 | 58.9 | 36.95 | 94.9 |
| p-Cresol | % Remaining Range | ++++ | + | – | ++ | ++++ |
| | % Remaining | <1% | 85% | 94% | 58% | <1% |
| | Material Test Conc. (mg/mL) | 37.7 | 42.4 | 43.3 | 34.5 | 41.7 |

Key to Tables 13 and 14

| Symbol | % Remaining |
|---|---|
| – | >93% |
| + | 65-93% |
| ++ | 35-65% |
| +++ | 10-35% |
| ++++ | <10% |

As seen in Table 13, the number of toxins adsorbed and the extent of adsorption of each toxin varied across materials tested in the assay. AB-2004 and activated charcoal each adsorbed >90% of the spiked 4-ethylphenol, 3-indoxyl sulfate and p-cresol in the assay, while cellulose acetate propionate adsorbed 65-90% of spiked 4-ethylphenol and to a 35-65% of p-cresol, but less than 10% of spiked 3-indoxyl sulfate. Bentonite adsorbed 35-65% of spiked 4-ethylphenol and 10-35% of spiked p-cresol in the assay, and <10% of spiked 3-indoxyl sulfate. Zeolite adsorbed 10-35% of spiked 4-ethylphenol in the assay, and less than 10% of spiked p-cresol and 3-indoxyl sulfate. Thus, different materials have different affinities for various toxins within the ex vivo assay, which recapitulates some of the diversity and composition of metabolites found in the human gut.

To determine the capacity of AB-2004, bentonite, zeolite and cellulose acetate propionate (Mn ~15,000) to adsorb the toxins 4-ethylphenyl sulfate and p-cresyl sulfate from a complex mixture of metabolites similar to those found in the lumen of the human colon, an ex vivo assay was performed using human stool. A freshly collected stool was maintained at or below 4° C. in an anaerobic chamber (AS-580, Anaerobe Systems, Morgan Hill, Calif.) with an atmosphere of 5% carbon dioxide, 5% hydrogen and balance nitrogen, the stool was suspended in ice-cold phosphate buffered saline by pipetting to achieve 20% w/v fecal slurry, solids were allowed to settle, and the supernatant was transferred to conical tubes on ice prior to transfer to an aerobic atmosphere and –80° C. All subsequent steps were performed aerobically. Frozen aliquots were thawed on ice, centrifuged at 21,000×g for 3 minutes, and supernatant was transferred to fresh tubes. 4-ethylphenyl sulfate and p-cresyl sulfate were prepared in dimethyl sulfoxide at 25 mg/mL and added to separate aliquots of the fecal slurry supernatant to a final concentration of 0.75 mg/mL, in triplicate. The spiked fecal slurry supernatants were added to the sequestrant materials consisting of an AB-2004 preparation, bentonite, zeolite, and cellulose acetate propionate (Mn-75,000) to achieve 12 mg/mL final of the sequestrant materials. The mixtures were incubated with vigorous mixing in conical tubes at 1700 rpm at room temperature for 1 hour and centrifuged at 12,000×g for 1 minute. The supernatant was transferred to fresh conical tubes and frozen at –80° C. prior to quantification of 4-ethylphenyl sulfate and p-cresyl sulfate by LC-MS/MS analysis against a surrogate matrix curve (Charles River, Worcester, Mass.). Results are shown in Table 14.

TABLE 14

Percent 4-ethylphenyl sulfate and p-cresyl sulfate remaining following 1 hour incubation with various materials

| | Percent Toxin Remaining | |
|---|---|---|
| Material | 4-Ethylphenyl Sulfate | p-Cresyl Sulfate |
| AB-2004 | ++ | +++ |
| Bentonite | – | – |
| Zeolite | – | – |
| Cellulose Acetate Propionate Mn~75,000 | – | + |

As seen in Table 14, AB-2004 demonstrated the greatest affinity for 4-ethylphenyl sulfate and p-cresyl sulfate of any of the tested materials. Cellulose Acetate Propionate adsorbed 7-35% of p-cresyl sulfate but less than 7% of 4-ethyl phenyl sulfate in the assay. Bentonite and Zeolite adsorbed less than 7% of 4-ethylphenyl sulfate and p-cresyl sulfate in the assay. Thus, the tested materials demonstrated a range of affinities for 4-ethylphenyl sulfate and p-cresyl sulfate within the ex vivo assay, which recapitulates some of the diversity and composition of metabolites found in the human gut.

Example 15

Modeling MIA in mice by injecting pregnant dams with the viral double-stranded RNA mimic poly(I:C) yields offspring that exhibit the core communicative, social, and stereotyped impairments relevant to ASD. Pregnant C57BL/6N mice are injected intraperitoneally on day E12.5 with saline or 20 mg/kg poly(I:C) according to methods described in Smith et al. (2007), *J. Neurosci.*, 27:10695-10702, which is hereby incorporated by reference in its entirety. MIA offspring and control offspring are either treated with an effective amount of an AB-2004 preparation daily for 10 days, or are left untreated for 10 days. Offspring are monitored for levels of 4-EP, 4-EPS, PC, PCS, 4-hydroxyphenylacetate, 2-hydroxy-2(4-hydroxyphenyl)acetate, homocitrulline, hydroxy indole and/or 3-indoxyl sulfate in blood, urine and feces. Levels of 4-EP, 4-EPS, PC, PCS, 4-hydroxyphenylacetate, 2-hydroxy-2(4-hydroxyphenyl)acetate, homocitrulline, hydroxy indole and/or 3-indoxyl sulfate are observed to be reduced in AB-2004 treated MIA offspring relative to untreated MIA offspring. The treated offspring are observed to have levels of 4-EP, 4-EPS, PC, PCS, 3-4-hydroxyphenylacetate, 2-hydroxy-2(4-hydroxyphenyl)acetate, homocitrulline, hydroxy indole and/or 3-indoxyl sulfate similar to, equivalent to, or reduced as compared to untreated offspring and/or healthy subjects.

MIA offspring and control offspring are also observed for behavioral symptoms of ASD as follows. Open field exploration involves mapping an animal's movement in an open arena to measure locomotion and anxiety. Untreated MIA offspring display decreased entries and time spent in the center of the arena, which is indicative of anxiety-like behavior. Treated MIA offspring and untreated control offspring show commensurate or equivalent amounts of entries and time spent in the center of the arena.

Prepulse inhibition (PPI) measures the ability of an animal to inhibit its startle in response to an acoustic tone when it is preceded by a lower-intensity stimulus. Deficiencies in PPI are a measure of impaired sensorimotor gating and are observed in several neurodevelopmental disorders, including autism. Untreated MIA offspring exhibit decreased PPI. Treated MIA offspring and untreated control offspring show normal PPI.

The marble burying test measures the propensity of mice to engage repetitively in a natural digging behavior that is not confounded by anxiety. Untreated MIA offspring display increased stereotyped marble burying compared to controls. Treated MIA offspring and untreated control offspring, show normal digging behavior.

Ultrasonic vocalizations are used to measure communication by mice, wherein calls of varying types and motifs are produced in different social paradigms. Untreated MIA offspring exhibit deficits in communication, as indicated by reduced number and duration of ultrasonic vocalizations produced in response to a social encounter. Treated MIA offspring and untreated control offspring show a normal number and duration of ultrasonic vocalizations produced in response to a social encounter.

The three-chamber social test is used to measure ASD-related impairments in social interaction. Untreated MIA offspring exhibit deficits in both sociability, or preference to interact with a novel mouse over a novel object, and social preference, or preference to interact with an unfamiliar versus a familiar mouse. Treated MIA offspring and untreated control offspring show normal social interaction.

In some experiments, an inoculant of bacteria comprising one or more of *Prevotella* species, *Bifido* bacteria species, *Parabacteriodes* species, (e.g., *P. merdae, P. distasonis*), *Faecalibacterium* species, (e.g., *F. prausnitzii*), *Eubacterium* species, *Coprococcus* species, *Lactobacillus reuteri*, *Lactobacillus rhamnosis*, *Bacteroides caccae*, *Bacteroides ovatus*, *Bacteroides fragilis*, *Bacteroides vulgatus*, and/or *Bacteroides thetaiotaomicron*, or any combination thereof, is administered before, during, or after administration of the sequestrant composition, and the effect of the added bacteria is determined.

Example 16

Fecal samples are obtained from human patients undergoing treatment with an AB-2004 preparation or cholestyramine. For each sample, the AB-2004 preparation or cholestyramine is recovered and compounds eluted from the AB-2004 or cholestyramine are assayed by GC-MS or MALDI-TOF mass spectrometry for the presence of any of the microbial metabolites (and host-generated modifications of these metabolites) listed herein. One or more of the microbial metabolites (and/or host-generated modifications of these metabolites) described herein is then recovered from the AB-2004 or cholestyramine, demonstrating that said microbial metabolites (and/or host-generated modifications of these metabolites) are bound or sequestered by AB-2004 or cholestyramine in humans in vivo. These results will also demonstrate the therapeutic efficacy of the methods described herein.

Example 17

MIA offspring are generated as described above in Example 15. MIA offspring and control offspring are either treated with AB-2004 daily for 10 days or left untreated for 10 days. Offspring are monitored for levels of 4-EP, 4-EPS, PC, PCS, 4-hydroxyphenylacetate, 2-hydroxy-2(4-hydroxyphenyl)acetate, homocitrulline, hydroxy indole and/or 3-indoxyl sulfate in blood, urine and feces. Levels of 4-EP, 4-EPS, PC, PCS, 4-hydroxyphenylacetate, 2-hydroxy-2(4-hydroxyphenyl)acetate, homocitrulline, hydroxy indole and/or 3-indoxyl sulfate are observed to be reduced in AB-2004 treated MIA offspring relative to untreated MIA offspring. The treated offspring are observed to have levels of 4-EP, 4-EPS, PC, PCS, 4-hydroxyphenylacetate, 2-hydroxy-2(4-hydroxyphenyl)acetate, homocitrulline, hydroxy indole and/or 3-indoxyl sulfate similar to, equivalent to, or reduced as compared to untreated offspring and/or healthy subjects.

MIA offspring and control offspring are also tested for leaky gut symptoms by orally administering oligosaccharides of large size, such as lactulose or high MW-PEGs (1500 or 4000 kD), and/or small sugars such as mannitol, L-rhamnose, or low MW-PEG (400 kD), and/or other indigestible probes such as $^{51}$Cr-EDTA. Administration of said compounds occurs separately from administration of AB-2004 or other sequestering agent. Urine is collected and monitored for the presence of such molecules, where the presence of the test molecule in the urine is symptomatic of leaky gut. Untreated MIA offspring show significant amounts of lactulose, high MW-PEGs (1500 or 4000 kD), small sugars, mannitol, L-rhamnose, low MW-PEG (400 kD), $^{51}$Cr-EDTA and/or other indigestible probes in their urine after oral administration. Treated MIA offspring and untreated control offspring show little or no lactulose, high MW-PEGs (1500 or 4000 kD), small sugars, mannitol, L-rhamnose, low MW-PEG (400 kD), $^{51}$Cr-EDTA and/or other indigestible probes in their urine after oral administration.

In some experiments, an inoculant of bacteria comprising one or more of *Prevotella* species, *Bifido* bacteria species, *Parabacteriodes* species, (e.g., *P. merdae, P. distasonis*), *Faecalibacterium* species, (e.g., *F. prausnitzii*), *Eubacterium* species, *Coprococcus* species, *Lactobacillus reuteri*, *Lactobacillus rhamnosis*, *Bacteroides caccae*, *Bacteroides*

*ovatus, Bacteroides fragilis, Bacteroides vulgatus,* and/or *Bacteroides thetaiotaomicron*, or any combination thereof, is administered before, during, or after administration of the sequestrant composition, and the effect of the added bacteria is determined.

Example 18

CNTNAP2$^{-/-}$ or Shank3$^{-/-}$ mice provide genetic models of autism-like behaviors. See, e.g., Welberg et al. (2011), *Nature Rev. Neurosci.*, 12:615 and Silverman et al. (2010), *Nature Rev. Neurosci.* 11:490-502, each of which is hereby incorporated by reference in its entirety. CNTNAP2$^{-/-}$, Shank3$^{-/-}$ or genetically unaltered (control) mice are either treated with AB-2004 or other sequestering agent daily for 10 days or left untreated for 10 days. Mice are monitored for levels of 4-EP, 4-EPS, PC, PCS, 4-hydroxyphenylacetate, 2-hydroxy-2(4-hydroxyphenyl)acetate, homocitrulline, hydroxy indole and/or 3-indoxyl sulfate in blood and feces. Levels of 4-EP, 4-EPS, PC, PCS, 4-hydroxyphenylacetate, 2-hydroxy-2(4-hydroxyphenyl)acetate, homocitrulline, hydroxy indole and/or 3-indoxyl sulfate are observed to be reduced in AB-2004 treated CNTNAP2$^{-/-}$ or Shank3-/- mice relative to untreated CNTNAP2$^{-/-}$ or Shank3$^{-/-}$ mice. The treated mice are observed to have levels of 4-EP, 4-EPS, PC, PCS, 4-hydroxyphenylacetate, 2-hydroxy-2(4-hydroxyphenyl)acetate, homocitrulline, hydroxy indole and/or 3-indoxyl sulfate similar to, equivalent to, or reduced as compared to untreated mice and/or healthy subjects. CNTNAP2$^{-/-}$ or Shank3$^{-/-}$ mice and control mice are also observed for behavioral symptoms of ASD as in Example 15.

In the open field exploration assay, untreated CNTNAP2$^{-/-}$ or Shank3$^{-/-}$ mice display decreased entries and time spent in the center of the arena, which is indicative of anxiety-like behavior. Treated CNTNAP2$^{-/-}$ or Shank3$^{-/-}$ mice and untreated control mice show commensurate or equivalent amounts of entries and time spent in the center of the arena.

In the prepulse inhibition (PPI) assay, untreated CNTNAP2$^{-/-}$ or Shank3$^{-/-}$ mice exhibit decreased PPI. Treated CNTNAP2$^{-/-}$ or Shank3$^{-/-}$ mice and untreated control mice show normal PPI.

In the marble burying assay, untreated CNTNAP2$^{-/-}$ or Shank3$^{-/-}$ mice display increased stereotyped marble burying compared to controls. Treated CNTNAP2$^{-/-}$ or Shank3$^{-/-}$ mice and untreated control offspring, show normal digging behavior.

In the ultrasonic vocalization assay, treated CNTNAP2$^{-/-}$ or Shank3$^{-/-}$ mice and untreated control mice show a normal number and duration of ultrasonic vocalizations produced in response to a social encounter.

In the three-chamber social test, untreated CNTNAP2$^{-/-}$ or Shank3$^{-/-}$ mice exhibit deficits in both sociability and social preference. Treated CNTNAP2$^{-/-}$ or Shank3$^{-/-}$ mice and untreated control mice show normal social interaction.

In some experiments, an inoculate of bacteria comprising one or more of *Prevotella* species, *Bifido* bacteria species, *Parabacteriodes* species, (e.g., *P. merdae, P. distasonis*), *Faecalibacterium* species, (e.g., *F. prausnitzii*), *Eubacterium* species, *Coprococcus* species, *Lactobacillus reuteri, Lactobacillus rhamnosis, Bacteroides caccae, Bacteroides ovatus, Bacteroides fragilis, Bacteroides vulgatus,* and/or *Bacteroides thetaiotaomicron*, or any combination thereof, is administered before, during, or after administration of the sequestrant composition, and the effect of the added bacteria is determined.

Example 19

Mecp2$^{-/-}$ or an equivalent mouse model of Rett Syndrome are evaluated for improvement in behavioral and/or gastrointestinal symptoms following treatment with an AB-2004 preparation or other sequestering agents. See, e.g., Shahbazian et al. (2002), *Neuron* 35:243-254, which is hereby incorporated by reference in its entirety. Mecp2$^{-/-}$ or equivalent mice, and genetically unaltered (control) mice are either treated with AB-2004 or other sequestering agent daily for 10 days or left untreated for 10 days. Mice are monitored for levels of 4-EP, 4-EPS, PC, PCS, 4-hydroxyphenylacetate, 2-hydroxy-2(4-hydroxyphenyl)acetate, homocitrulline, hydroxy indole and/or 3-indoxyl sulfate in blood, urine and feces. Levels of 4-EP, 4-EPS, PC, PCS, 4-hydroxyphenylacetate, 2-hydroxy-2(4-hydroxyphenyl)acetate, homocitrulline, hydroxy indole and/or 3-indoxyl sulfate are observed to be reduced in AB-2004 treated Mecp2$^{-/-}$ or an equivalent mice relative to untreated Mecp2$^{-/-}$ or equivalent mice. The treated mice are observed to have levels of 4-EP, 4-EPS, PC, PCS, 4-hydroxyphenylacetate, 2-hydroxy-2(4-hydroxyphenyl)acetate, homocitrulline, hydroxy indole and/or 3-indoxyl sulfate similar to, equivalent to, or reduced as compared to untreated mice and/or healthy subjects. Mecp2$^{-/-}$ or equivalent mice and control mice are also observed for behavioral symptoms of ASD as in Example 15.

In the open field exploration assay, untreated Mecp2$^{-/-}$ or equivalent mice display decreased entries and time spent in the center of the arena, though fecal bolus counts, grooming times, and time spent in different areas of the field may not be affected. Treated Mecp2-/- or an equivalent mice and untreated control mice show commensurate or equivalent amounts of entries and time spent in the center of the arena. Untreated Mecp2$^{-/-}$ or equivalent mice also show inertia, breathing irregularities, and hind limb clasping phenotypes not present in treated Mecp2$^{-/-}$ or equivalent mice or in control mice.

Mecp2$^{-/-}$ or equivalent mice and control mice are also tested for leaky gut symptoms by orally administering oligosaccharides of large size, such as lactulose or high MW-PEGs (1500 or 4000 kD), and/or small sugars such as mannitol, L-rhamnose, or low MW-PEG (400 kD), and/or other indigestible probes such as $^{51}$Cr-EDTA. Administration of said compounds occurs separately from administration of AB-2004 or other sequestering agent. Urine is collected and monitored for the presence of such molecules, where the presence of the test molecule in the urine is symptomatic of leaky gut. Untreated Mecp2-/- or equivalent mice show significant amounts of lactulose, high MW-PEGs (1500 or 4000 kD), small sugars, mannitol, L-rhamnose, low MW-PEG (400 kD), $^{51}$Cr-EDTA and/or other indigestible probes in their urine after oral administration. Treated Mecp2-/- or equivalent mice and untreated control mice show little or no lactulose, high MW-PEGs (1500 or 4000 kD), small sugars, mannitol, L-rhamnose, low MW-PEG (400 kD), $^{51}$Cr-EDTA and/or other indigestible probes in their urine after oral administration.

In some experiments, an inoculant of bacteria comprising one or more of *Prevotella* species, *Bifido* bacteria species, *Parabacteriodes* species, (e.g., *P. merdae, P. distasonis*), *Faecalibacterium* species, (e.g., *F. prausnitzii*), *Eubacterium* species, *Coprococcus* species, *Lactobacillus reuteri,*

*Lactobacillus rhamnosis, Bacteroides caccae, Bacteroides ovatus, Bacteroides fragilis, Bacteroides vulgatus,* and/or *Bacteroides thetaiotaomicron*, or any combination thereof, is administered before, during, or after administration of the sequestrant composition, and the effect of the added bacteria is determined.

Example 20

We have previously generated bacterial strains that produce 4-ethylphenol (4-EP) (the precursor to 4-EPS) and colonized mice with these strains, and have shown that intestinal production of a specific microbial metabolite is sufficient to promote anxiety and related behaviors in mice. Anxiety can also be induced by injection of 4-EPS.

Animals and Dosing

In the present study, 3-week-old microbiologically sterile (germ-free) and normally colonized specific pathogen free (SPF), C57Bl/6 mice are obtained (Jackson Labs, Bar Harbor, Me.). Mice are initially divided into 4 groups: 1) specific pathogen free; 2) germ-free; 3) germ-free colonized with engineered bacterial strains that produce 4-EP or, alternatively, germ-free injected intravenously with 4-EPS; 4) germ-free colonized with engineered bacterial strains that do not produce 4-EP. Each group is further divided into groups that are administered an AB-2004 preparation, saline (negative control), *B. fragilis* (positive control), and no treatment. Each test article is administered orally, once per day or at each feeding. The test articles are administered for five weeks, followed by behavioral testing. In some groups, dosing is discontinued prior to behavioral testing, and in some groups dosing continues throughout the testing period.

An AB-2004 preparation (AST-120, Kureha Corporation, Japan) is given in food or by gavage, *B. fragilis* at $10^{10}$ cfu in 1.5% sodium bicarbonate solution is administered in apple sauce plugs or by gavage, and saline is administered in food or by gavage. The AB-2004 preparation is initially dosed at a level of 8-100 mg/mouse/dose and dosing is adjusted as necessary.

Behavioral Testing

In the elevated "plus" maze test, animals are placed on an apparatus having two crossed elements in the shape of a plus-sign, with one element enclosed and one element exposed. Animals having symptoms of anxiety spend more time in the enclosed regions of the maze relative to animals without anxiety. In the present study, mice colonized with 4-EP producing bacteria and treated with AB-2004, mice colonized with 4-EP producing bacteria and treated with *B. fragilis*, and mice that are not colonized by 4-EP producing bacteria (specific pathogen free, germ-free, and germ-free colonized with engineered bacterial strains that do not produce 4-EP), spend less time in the enclosed regions of the maze relative to untreated mice or mice colonized with 4-EP producing bacteria that are mock-treated with saline, indicating a reduction in anxiety symptoms due to the AB-2004 or *B. fragilis* treatment.

In the light/dark box test, animals are placed in a box, most of which is lit, with a smaller separate dark compartment accessible to the animal. Mice showing symptoms of anxiety spend less time in the lit areas of the box relative to animals without anxiety. In the present study, mice colonized with 4-EP producing bacteria and treated with AB-2004, mice colonized with 4-EP producing bacteria and treated with *B. fragilis*, and mice that are not colonized by 4-EP producing bacteria (specific pathogen free, germ-free, and germ-free colonized with engineered bacterial strains that do not produce 4-EP), spend less time in the enclosed regions relative to untreated mice or mice colonized with 4-EP producing bacteria that are mock-treated with saline, indicating a reduction in anxiety symptoms due to the AB-2004 or *B. fragilis* treatment.

The open field exploration assay is described in Example 15. In the present study, mice colonized with 4-EP producing bacteria and treated with AB-2004, mice colonized with 4-EP producing bacteria and treated with *B. fragilis*, and mice that are not colonized by 4-EP producing bacteria (specific pathogen free, germ-free, and germ-free colonized with engineered bacterial strains that do not produce 4-EP), show more entries into the center of the arena and spend more time in the center of the arena relative to untreated mice or mice colonized with 4-EP producing bacteria that are mock-treated with saline, indicating a reduction in anxiety symptoms due to the AB-2004 or *B. fragilis* treatment.

Non-Behavioral Testing

Levels of pro-inflammatory markers, including IL-6, TNF-$\alpha$, etc., are evaluated in tissue after sacrifice. Elevated levels of pro-inflammatory markers are seen in mice colonized with 4-EP producing bacteria and treated with an AB-2004 preparation, mice colonized with 4-EP producing bacteria and treated with *B. fragilis*, and mice that are not colonized by 4-EP producing bacteria (specific pathogen free, germ-free, and germ-free colonized with engineered bacterial strains that do not produce 4-EP) relative to untreated mice or mice colonized with 4-EP producing bacteria that are mock-treated with saline, indicating a reduction in inflammatory responses due to the AB-2004 or *B. fragilis* treatment.

Serum and urine levels of key microbial metabolites including 4-EP, 4-EPS, PC, PCS, 4-hydroxyphenylacetate, 2-hydroxy-2(4-hydroxyphenyl)acetate, homocitrulline, indole pyruvate, serotonin, 3-hydroxy indole and indoxylsulfate will be monitored during dosing and before behavior tests as early indicator of sequestration. Dosing can be adjusted in order to provide additional reductions in metabolite levels. Reduced levels of anxiety-associated metabolites are seen in mice colonized with 4-EP producing bacteria and treated with an AB-2004 preparation, mice colonized with 4-EP producing bacteria and treated with *B. fragilis*, and mice that are not colonized by 4-EP producing bacteria (specific pathogen free, germ-free, and germ-free colonized with engineered bacterial strains that do not produce 4-EP) relative to untreated mice or mice colonized with 4-EP producing bacteria that are mock-treated with saline, indicating a reduction in metabolite levels due to the AB-2004 or *B. fragilis* treatment.

In some experiments, an inoculant of bacteria comprising one or more of *Prevotella* species, *Bifido* bacteria species, *Parabacteriodes* species, (e.g., *P. merdae, P. distasonis*), *Faecalibacterium* species, (e.g., *F. prausnitzii*), *Eubacterium* species, *Coprococcus* species, *Lactobacillus reuteri, Lactobacillus rhamnosis, Bacteroides caccae, Bacteroides ovatus, Bacteroides vulgatus,* and/or *Bacteroides thetaiotaomicron*, or any combination thereof, is administered rather than *B. fragilis*.

Example 21

The effect of AB-2004 was studied in gnotobiotic mice that had been colonized with one or more specific bacterial strains, or with human fecal matter, that had previously been characterized to produce one or more intestinal metabolites associated with the microbially produced metabolites (or host-modifications thereof) described herein, including 4-ethylphenol (4-EP), p-cresol (PC), 3-hydroxy indole, 4-ethylphenyl sulfate (4-EPS), p-cresyl sulfate (PCS), and 3-indoxyl sulfate. The effect of AB-2004, a material that sequesters one or more intestinal metabolites associated with the microbially produced metabolites (or host-modifications thereof) described herein, including 4-ethylphenol (4-EP), p-cresol (PC), 3-hydroxy indole, 4-ethylphenyl sulfate (4-EPS), p-cresyl sulfate (PCS), and 3-indoxyl sulfate, was investigated by formulating AB-2004 into mouse food and administering it in parallel with a control diet that did not contain AB-2004 but was otherwise identical. Impact of toxic microbial metabolite production by the microbiota and AB-2004 administration was determined via assessments of the levels of the toxic bacterial metabolites in samples of serum, feces and/or urine obtained from the host, impact on repetitive, social, sensory and anxiety-like behaviors that represent core and non-core symptoms of autism spectrum disorders (ASD), and impact on the integrity of gastrointestinal barrier as a measure of leaky gut.

At 4 weeks of age and after weaning gnotobiotic mice were colonized with either specific bacterial strains or with human fecal matter. At the age of 5 weeks, mice were placed on a diet that contained 8% w/w AB-2004, or an otherwise identical diet that did not contain AB-2004. Colonization of mice was confirmed by plating dilutions of fecal homogenates on solid media and assessment of bacterial strain specific markers.

Marble Burying

A marble burying test was used to assess repetitive behavior, which is a core symptom of ASD. In the assay as described by Malkova et al. (*Behav Immun.* 26(4):607-16 (2012)), marbles are placed on top of bedding in a cage, a test mouse is placed in the cage, and the number of marbles buried by the mouse during the test period is measured. Mice given control diet that were colonized with specific bacterial strains, or with human fecal matter, that produce toxic metabolites buried significantly more marbles than germ free gnotobiotic mice, thereby demonstrating repetitive behavior due to toxic bacterial metabolite production by the gut microbiota. Administration of AB-2004 to mice colonized with specific bacterial strains, or with human fecal matter, that produce toxic metabolites normalized this repetitive behavior in the assay. The data indicate that administration of materials that sequester 4-EP, PC, 3-hydroxy indole, 4-EPS, PCS, and 3-indoxyl sulfate, can be beneficial for reducing repetitive behaviors, one of the core symptoms of ASD, in some ASD patients.

Elevated Plus Maze

The elevated plus maze (EPM) test of exploratory behavior was used to assess general locomotion and anxiety-like behavior. Mice were allowed 5 minutes to explore an elevated plus maze comprised of two open arms and two closed arms that extend from a common central platform. A small raised lip around the edges of the open arms helped prevent mice from slipping off. An overhead video camera was used to record the session, and Ethovision software (Noldus Information Technology, Sacramento, Calif.) was used to analyze mouse movements. Time spent in closed, relatively protected portions of the maze versus time spent exploring open, relatively exposed portions of the maze is interpreted as a measurement of anxiety. Mice given control diet that were colonized with specific bacterial strains, or with human fecal matter, that produce toxic metabolites spent significantly less time in the open portions of the EPM versus closed portions of the EPM than germ free gnotobiotic mice. Thereby demonstrating anxiety-like behavior due to production of toxic metabolites by the intestinal microbiota. Administration of AB-2004 normalized these anxiety-like behaviors in the assay. Anxiety is a common non-core symptom of ASD, and these data indicate that administration of sequestrants of 4-EP, PC, 3-hydroxy indole, 4-EPS, PCS, and 3-indoxyl sulfate can be beneficial in reducing anxiety in some ASD patients.

Open Field

The open field test of exploratory behavior was used to assess general locomotion and anxiety-like behavior. For open-field testing, mice were allowed to explore a 50×50-cm white Plexiglas box for 10 min. An overhead video camera was used to record the session, and Ethovision software (Noldus Information Technology, Sacramento, Calif.) was used to analyze the distance traveled, and the number of entries and duration of time spent in the center arena (central square, 17×17 cm) versus the wall area of the box. Mice given control diet that were colonized with specific bacterial strains, or with human fecal matter, that produce toxic metabolites exhibited an anxiety-like phenotype in this assay, spending less time within and crossing the center of the test arena, entering the wall area with greater frequency and spending more time in the wall area when compared with germ free gnotobiotic mice. Administration of AB-2004 normalized these anxiety-like behaviors in the assay. Importantly, total distance moved in the open field test was similar for all groups, suggesting that differences in exploration of open versus closed parts of the field are not due to differences in the distance that the mice moved during the test. Consistent with the EPM data, these data provide additional evidence that administration of materials that sequester 4-EP, PC, 3-hydroxy indole, 4-EPS, PCS, and 3-indoxyl sulfate can be beneficial in alleviating symptoms of anxiety in ASD patients who suffer from them.

Direct Social Interaction

A three-chambered social approach test was used to measure direct social interaction. The test mouse was placed in the center chamber of three adjacent chambers, with a novel object in an adjacent terminal chamber and an unfamiliar mouse in the other adjacent terminal chamber. The test mouse was habituated in the apparatus for 10 minutes prior to initiation of scoring. The test mouse was able to pass through openings from the center chamber into each of the adjacent chambers. The test was recorded by video, and the time spent by the test mouse in the chamber with the unfamiliar mouse was scored manually. A higher amount of time spent with the unfamiliar mouse is an indicator of increased sociability, while a lower amount of time spent with the unfamiliar mouse is an indicator of decreased sociability, consistent with the social deficits that are a core symptom of Autism Spectrum Disorders.

In this test of social interaction, male mice colonized with specific bacterial strains, or with human fecal matter, that produce toxic metabolites spent significantly less time in the chamber with another mouse than male germ free gnotobiotic mice. Administration of AB-2004 normalized the deficits in social behavior observed in the assay. These data indicate that administration of materials such as AB-2004 that sequester 4-EP, PC, 3-hydroxy indole, 4-EPS, PCS, and 3-indoxyl sulfate can be beneficial to improve core symptoms of ASD, such as social deficits.

Sensory Gating

Prepulse inhibition (PPI) measures the ability of an animal to inhibit its startle in response to an acoustic tone when it is preceded by a lower-intensity stimulus. Deficiencies in PPI are a measure of impaired sensorimotor gating and are observed in several neurodevelopmental disorders, including autism. Mice colonized with specific bacterial strains, or with human fecal matter, that produce toxic metabolites exhibit decreased PPI response in comparison to that observed in germ free gnotobiotic mice. Administration of AB-2004 normalized the deficits in sensory gating observed in the assay.

Social Communication Behavior

Ultrasonic vocalizations are used to measure social communication by mice, wherein calls of varying types and motifs are produced in different social paradigms. Mice colonized with specific bacterial strains, or with human fecal matter, that produce toxic metabolites exhibit deficits in communication, as indicated by reduced number and duration of ultrasonic vocalizations produced in response to a social encounter. Administration of AB-2004 normalized the deficits in social communication behavior observed in the assay.

Social Interaction Behavior

The three-chamber social test is used to measure ASD-related impairments in social interaction. Mice colonized with specific bacterial strains, or with human fecal matter, that produce toxic metabolites exhibit deficits in both sociability, or preference to interact with a novel mouse over a novel object, and social preference, or preference to interact with an unfamiliar versus a familiar mouse. Administration of AB-2004 normalized the deficits in social interaction behavior observed in the assay.

Gastrointestinal Barrier Integrity

Mice colonized with specific bacterial strains, or with human fecal matter, that produce toxic metabolites were also tested for leaky gut symptoms by orally administering oligosaccharides of large size, such as lactulose or high MW-PEGs (1500 or 4000 kD), and/or small sugars such as mannitol, L-rhamnose, or low MW-PEG (400 kD), and/or other indigestible probes such as 51Cr-EDTA. Urine, blood and/or fecal samples are collected and monitored for the presence of such molecules, where the presence of the test molecule in the urine is symptomatic of leaky gut. Mice colonized with specific bacterial strains, or with human fecal matter, that produce toxic metabolites show significant amounts of lactulose, high MW-PEGs (1500 or 4000 kD), small sugars, mannitol, L-rhamnose, low MW-PEG (400 kD), 51Cr-EDTA and/or other indigestible probes in their urine after oral administration. Administration of AB-2004 normalized one or more of the elevated urine levels lactulose, high MW-PEGs (1500 or 4000 kD), small sugars, mannitol, L-rhamnose, low MW-PEG (400 kD), 51Cr-EDTA and/or other indigestible probes, indicating a correction of leaky gut.

Serum, Urine and Feces

Levels of key microbial metabolites including 4-ethylphenol (4-EP), p-cresol (PC), 3-hydroxy indole, 4-ethylphenyl sulfate (4-EPS), p-cresyl sulfate (PCS), 3-indoxyl sulfate, indole pyruvate and/or serotonin were monitored as an indicator of sequestration. Dosing may be adjusted in order to provide additional reductions in metabolite levels. In mice colonized with specific bacterial strains, or with human fecal matter, that produce toxic metabolites, treatment with AB-2004 reduced levels of one or more of these target metabolites.

With respect to the use of substantially any plural and/or singular terms herein, those having skill in the art can translate from the plural to the singular and/or from the singular to plural as is appropriate to the context and/or application. The various singular/plural permutations can be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of treating a subject having a behavioral symptom of a neurological disorder associated with autism spectrum disorder, comprising:
   administering to the subject a therapeutically effective amount of an activated carbon sequestrant composition which binds to at least a fraction of at least one intestinal metabolite present in the digestive tract of the subject to form a sequestrant-metabolite complex, such that the sequestrant-metabolite complex is eliminated from the digestive tract;
   wherein the at least one intestinal metabolite is 4-ethylphenol and the behavioral symptom is clinical irritability;
   wherein the sequestrant composition comprises a multiplicity of biocompatible particles which are non-absorbable by the digestive tract of the subject;
   wherein the therapeutically effective amount is 35 mg to 35 g per day;
   and wherein the therapeutically effective amount alleviates the clinical irritability.

2. The method of claim 1, wherein the subject is identified as having autism spectrum disorder.

3. The method of any one of claim 1 or 2, wherein the subject does not have chronic kidney disease.

4. The method of any one of claim 1 or 2, or wherein the subject does not have clinical anxiety or an anxiety disorder.

5. The method of any one of claim 1 or 2, wherein the sequestrant composition binds to at least a portion of an additional intestinal metabolite present in the digestive tract of the subject to form a sequestrant-metabolite complex, such that the sequestrant-metabolite complex is eliminated from the digestive tract, and wherein the additional metabolite is selected from the group consisting of: 4-ethylphenylsulfate (4-EPS), p-cresol (PC), p-cresyl sulfate (PCS), 3-hydroxy indole, and 3-indoxyl sulfate.

6. The method of any one of claim 1 or 2, wherein: the sequestrant composition comprises an AB-2004 preparation comprising spherical activated carbon particles having a minimum average specific surface area determined by the Brunauer-Emmett-Teller (BET) method of at least 500 $m^2/g$ and a maximum average specific surface area determined by the Brunauer-Emmett-Teller (BET) method less than 4000 $m^2/g$.

7. The method of claim 5, wherein the sequestrant composition comprises an AB-2004 preparation comprising spherical activated carbon particles having a minimum average particle diameter of at least 0.005 mm and a maximum average particle diameter of less than 1.5 mm.

8. The method of any one of claim 1 or 2, further comprising monitoring intestinal metabolite levels of the subject during a course of treatment.

9. The method of any one of claim 1 or 2, further comprising monitoring changes in the behavioral symptom of the subject.

10. The method of any one of claim 1 or 2, wherein the sequestrant composition is administered following appearance of the behavioral symptom of the neurological disorder.

11. The method of any one of claim 1 or 2, wherein the method is repeated as necessary to maintain reduced levels of intestinal metabolites relative to levels identified prior to first administration of the sequestrant composition.

12. The method of claim 1 wherein, the therapeutically effective amount is 5 mg/kg to 500 mg/kg of body weight per day.

13. The method of claim 2 wherein, the therapeutically effective amount is 5 mg/kg to 500 mg/kg of body weight per day.

14. The method of claim 3 wherein, the therapeutically effective amount is 5 mg/kg to 500 mg/kg of body weight per day.

15. The method of claim 4 wherein, the therapeutically effective amount is 5 mg/kg to 500 mg/kg of body weight per day.

16. The method of claim 5 wherein, the therapeutically effective amount is 5 mg/kg to 500 mg/kg of body weight per day.

17. The method of claim 6 wherein, the therapeutically effective amount is 5 mg/kg to 500 mg/kg of body weight per day.

18. The method of claim 7 wherein,
   the therapeutically effective amount is 5 mg/kg to 500 mg/kg of body weight per day.

19. The method of claim 8 wherein, the therapeutically effective amount is 5 mg/kg to 500 mg/kg of body weight per day.

20. The method of claim 9 wherein, the therapeutically effective amount is 5 mg/kg to 500 mg/kg of body weight per day.

21. The method of claim 10 wherein, the therapeutically effective amount is 5 mg/kg to 500 mg/kg of body weight per day.

22. The method of claim 12 wherein, the therapeutically effective amount is 5 mg/kg to 500 mg/kg of body weight per day.

* * * * *